(12) United States Patent
Noguchi

(10) Patent No.: US 7,020,245 B2
(45) Date of Patent: Mar. 28, 2006

(54) MULTILEAF COLLIMATOR

(75) Inventor: Tadashi Noguchi, Tochigi-ken (JP)

(73) Assignees: Kabushiki Kaisha Toshiba, Tokyo (JP); Toshiba Medical Systems Corporation, Otawara (JP)

( * ) Notice: Subject to any disclaimer, the term of this patent is extended or adjusted under 35 U.S.C. 154(b) by 39 days.

(21) Appl. No.: 10/799,774

(22) Filed: Mar. 15, 2004

(65) Prior Publication Data

US 2004/0240621 A1 Dec. 2, 2004

(30) Foreign Application Priority Data

Mar. 13, 2003 (JP) ............................ 2003-067559

(51) Int. Cl.
*G21K 1/04* (2006.01)

(52) U.S. Cl. ..................... 378/150; 378/65; 378/206

(58) Field of Classification Search ........ 378/147–153, 378/206, 65
See application file for complete search history.

(56) References Cited

U.S. PATENT DOCUMENTS

| | | | | |
|---|---|---|---|---|
| 4,628,523 A * | 12/1986 | Heflin | ......................... | 378/193 |
| 4,868,843 A | 9/1989 | Nunan | ......................... | 378/152 |
| 4,882,741 A | 11/1989 | Brown | ........................ | 378/152 |
| 4,891,833 A * | 1/1990 | Bernardi | ...................... | 378/145 |
| 5,012,506 A | 4/1991 | Span et al. | .................. | 378/152 |
| 6,600,810 B1 * | 7/2003 | Hughes | ........................ | 378/152 |
| 6,795,523 B1 * | 9/2004 | Steinberg | ...................... | 378/65 |

* cited by examiner

*Primary Examiner*—Craig E. Church
*Assistant Examiner*—Jurie Yun
(74) *Attorney, Agent, or Firm*—Oblon, Spivak, McClelland, Maier & Neustadt, P.C.

(57) ABSTRACT

A collimating device for controlling a radiation field of an X-ray radiated from an X-ray radiator. The device includes a plurality of first collimating leaves, a plurality of second collimating leaves, a beam generator, a detector, a memory, and a controller. The plurality of second collimating leaves oppose the first collimating leaves. The beam generator is configured to generate a beam. The beam emanates between the first collimating leaves and the second collimating leaves. The detector is configured to detect the beam. The memory is configured to store position information of each leaf of the first and second collimating leaves when the each leaf is determined to intersect the beam based on the detection. The controller is configured to position the each leaf based on the position information so as to control the radiation field.

20 Claims, 21 Drawing Sheets

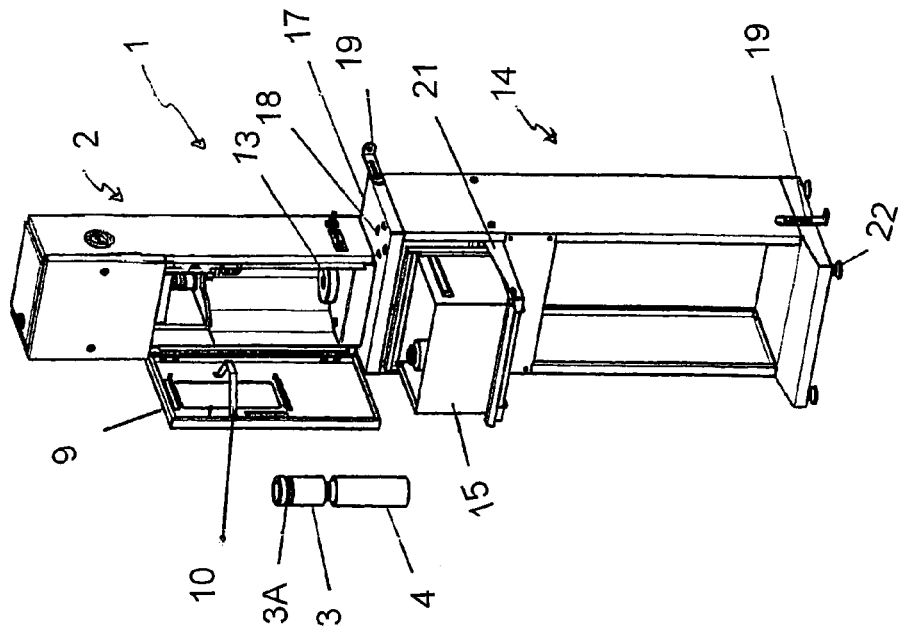
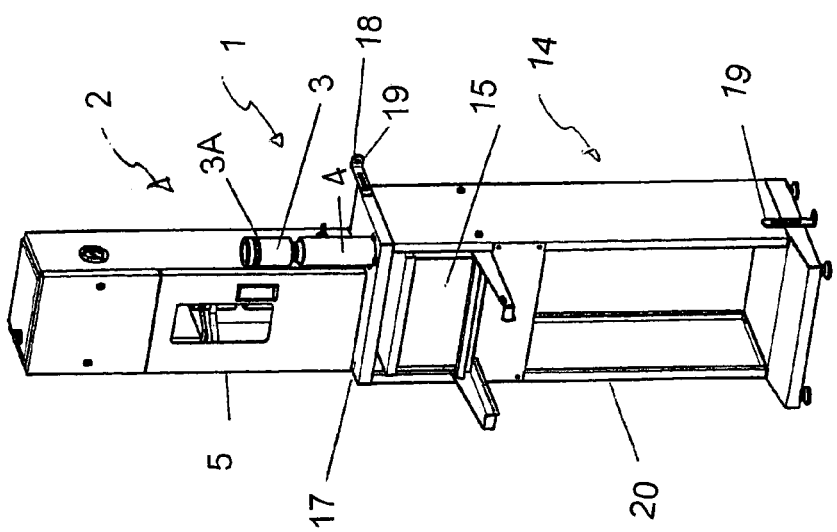

MULTILEAF COLLIMATOR

CROSS-REFERENCE TO RELATED APPLICATION

This application is based upon and claims the benefit of priority from prior Japanese Patent Application No. P2003-67559, filed on Mar. 13, 2003, the entire contents of which is hereby incorporated herein by reference.

BACKGROUND OF THE INVENTION

1. Field of the Invention

The present invention relates to a collimator which is used in a radiotherapy apparatus and controls a radiation field by a plurality of collimating leaves. The present invention also relates to a method of positioning a plurality of collimating leaves of the collimator.

2. Discussion of the Background

It is important to reduce X-ray exposure to an object such as a patient when a radiotherapy apparatus or an X-ray diagnosis apparatus is used. Many types of techniques are presented for accomplishing the X-ray exposure reduction. One well-known technique is the use of a collimator. The collimator narrows a radiation field by reducing its aperture size. The aperture size is controllable by adjusting positions of aperture blades in intercrossing (X-Y) directions. The aperture blades are typically made of an X-ray non-transmission material such as lead or tungsten. In one example of the collimator, a lamp is provided at a position corresponding to an X-ray radiator. A shade resulting from the lamp light through the controlled aperture of the collimator is used for adjusting and determining an actual radiation field. In other words, a desired radiation field is obtained by controlling the aperture so that the shade is identical to the desired radiation field. This technique is disclosed, for example, in Japanese Patent Application Disclosure PH3-44768.

In many cases, however, a multileaf collimator is used for a radiotherapy apparatus. The multileaf collimator includes an arrangement of a plurality of collimating leaves formed in a mutually contiguous manner. The collimating leaves perform a function similar to that of the aperture blades. Instead of a pair of aperture blades, a pair of collimating members each of which include a plurality of collimating leaves are used in one direction for controlling the aperture so as to help form the shape of the aperture more appropriately to the shape of a tumor. If, however, the above-mentioned lamp is used to adjust a plurality of collimating leaves, it is not easy to obtain sufficient accuracy in terms of position adjustment. The position adjustment is usually performed at a position of the isocenter within a light emission field of the lamp. The required accuracy at the isocenter is, for example, one millimeter error. Meanwhile, a position of the collimating leaf is typically detected to the precision of 0.1 millimeter. Therefore, the detection error (i.e., incorrect detection result) of the collimating leaf position may lead to an error expansion at the isocenter. In other words, a slight detection error may result in an error beyond the required accuracy at the isocenter. Consequently, a high accuracy in the position detection is required for the collimating leaves.

SUMMARY OF THE INVENTION

According to a first aspect of the present invention, there is provided a collimating device for controlling the radiation field of an X-ray radiated from an X-ray radiator. The device includes a plurality of first collimating leaves, a plurality of second collimating leaves, a beam generator, a detector, a memory, and a controller. The plurality of second collimating leaves oppose the first collimating leaves. The beam generator is configured to generate a beam which emanates between the first plurality of collimating leaves and the second plurality of collimating leaves. The detector is configured to detect the beam. The memory is configured to store position information of each leaf of the first and second plurality of collimating leaves when each leaf is determined to intersect the beam based on the detection. The controller is configured to position each leaf based on the position information so as to control the radiation field.

According to a second aspect of the present invention, there is provided a collimating device for controlling a radiation field of an X-ray radiated from an X-ray radiator. The device includes a plurality of first collimating leaves, a plurality of second collimating leaves, a beam generator, a detector, a memory, and a controller. The plurality of second collimating leaves oppose the first collimating leaves. The beam generator is configured to generate at least first and second beams. The first beam intersects the first plurality of collimating leaves. The second beam intersects the second plurality of collimating leaves. The detector is configured to detect the first and second beams. The memory is configured to store first position information of each leaf of the first plurality of collimating leaves when each leaf is determined to intersect the first beam based on the detection. The memory is also configured to store second position information of each leaf of the second plurality of collimating leaves when each leaf is determined to intersect the second beam based on the detection. The controller is configured to position the each leaf of the first plurality of collimating leaves based on the first position information and each leaf of the second plurality of collimating leaves based on the second position information so as to control the radiation field.

According to a third aspect of the present invention, there is provided a radiotherapy apparatus for radiating an X-ray and concentrating the X-ray towards a predetermined part of an object. The apparatus includes an X-ray radiator and a collimator. The X-ray radiator is configured to radiate the X-ray. The collimator is configured to control a radiation field of the X-ray radiated by the X-ray radiator. The collimator includes a plurality of first collimating leaves, a plurality of second collimating leaves, a beam generator, a detector, a memory, and a controller. The plurality of second collimating leaves oppose the first collimating leaves. The beam generator is configured to generate a beam. The beam emanates between the first plurality of collimating leaves and the second plurality of collimating leaves. The detector is configured to detect the beam. The memory is configured to store position information of each leaf of the first and second plurality of collimating leaves when each leaf is determined to intersect the beam based on the detection. The controller is configured to position each leaf based on the position information.

According to a fourth aspect of the present invention, there is provided a method of positioning collimating leaves for use in a collimator which controls a radiation field of an X-ray radiated from an X-ray radiator. The collimating leaves include a plurality of first collimating leaves and a plurality of second collimating leaves opposing the first collimating leaves. The method begins by generating a beam which emanates between the first plurality of collimating leaves and the second plurality of collimating leaves. The method continues by detecting the beam and storing position information of each leaf of the first and second plurality of collimating leaves when each leaf is determined to intersect the beam based on the detection. The method further continues by positioning each leaf based on the position information so as to control the radiation field.

According to a fifth aspect of the present invention, there is provided a method of positioning collimating leaves for use in a collimator which controls a radiation field of an X-ray radiated from an X-ray radiator. The collimating leaves include a plurality of first collimating leaves and a plurality of second collimating leaves opposing the first collimating leaves. The method begins by generating at least first and second beams. The first beam intersects the first plurality of collimating leaves and the second beam intersects the second plurality of collimating leaves. The method continues by detecting the first and second beams and storing first position information of each leaf of the first plurality of collimating leaves when each first collimating leaf is determined to intersect the first beam based on the detection and second position information of each leaf of the second plurality of collimating leaves when each second collimating leaf is determined to intersect the second beam based on the detection. The method further continues by positioning each first collimating leaf based on the first position information and each second collimating leaf based on the second position information so as to control the radiation field.

BRIEF DESCRIPTION OF THE DRAWINGS

A more complete appreciation of embodiments of the present invention and many of its attendant advantages will be readily obtained by reference to the following detailed description considered in connection with the accompanying drawings, in which:

FIG. 1 is an illustration showing an example of a situation when a radiotherapy apparatus is used according to the first embodiment of the present invention;

FIG. 2 is an illustration showing an exemplary configuration of a collimator viewed from a first direction according to the first embodiment of the present invention;

DESCRIPTION OF THE PREFERRED EMBODIMENTS

Figure 4:
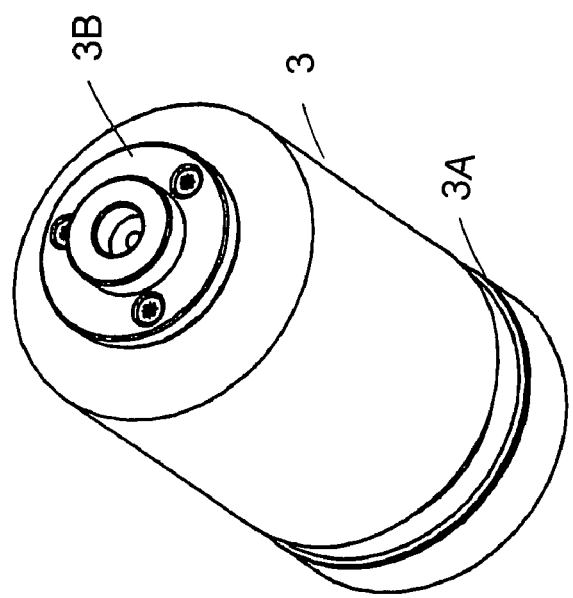
FIG. 4 is an illustration showing an example of a relationship between a tumor and an aperture of the collimator according to the first embodiment of the present invention.

Embodiments of the present invention will be described with reference to the accompanying drawings.

FIG. 1 is an illustration showing an example of a situation when a radiotherapy apparatus is used according to the first embodiment of the present invention. As shown in FIG. 1, a radiotherapy apparatus includes a radiation apparatus 10, a patient couch 20, and a controller 30. The radiation apparatus is used for radiating an X-ray towards an object such as a patient P. The patient couch 20 is used for positioning the patient P so that the radiated X-ray is exposed to a tumor of the patient P. The controller 30 is used for organically controlling units and apparatuses of the radiotherapy apparatus including the radiation apparatus 10 and the patient couch 20.

The radiation apparatus 10 includes a fixed gantry 11, a rotation gantry 12, a radiation head 13, and a collimator 14. The fixed gantry 11 is fixed on the floor. The rotation gantry 12 is rotatablly supported by the fixed gantry 1.1 The radiation head 13 includes an X-ray radiator and is provided in a body extended from one end of the rotation gantry 12. The collimator 14 is incorporated in the radiation head 13. The rotation gantry 12 is nearly 360 degrees rotatable around a horizontal axis H of the fixed gantry 11. The collimator 14 is rotatable around an X-ray axis I radiated from the radiation head 13. An intersection of the axes I and H is called an isocenter IC. The isocenter is, for example, determined at a position one meter from the X-ray radiator. The rotation gantry 12 can be used at a predetermined fixed position in the radiation and/or configured to rotate so as to enable various types of radiations, such as, for example, a rotation radiation, a pendulum radiation, and an intermittent radiation.

The patient couch 20 is rotatable along an arc centered on the axis I in a direction G within a predetermined angle range. The patient couch 20 includes an upper mechanism 21, a table 22, an elevator mechanism 23, and a bottom mechanism 24. The upper mechanism 21 supports the table 22 where the patient Plies. The upper mechanism 21 has a mechanism for moving the table 22 in directions e (i.e., head-foot directions of the patient P) and directions f (i.e., right-left directions of the patient P).

The upper mechanism 21 is supported by the elevator mechanism 23. The elevator mechanism 23 may be formed by link mechanics and be configured to move up and down in direction d, as shown. Accordingly, the elevator mechanism 23 raises and lowers the upper mechanism 21 and the table 22 within a predetermined range. This elevator mechanism 23 is supported by the bottom mechanism 24. The bottom mechanism 24 has a rotation mechanism which rotates the elevator mechanism 23 around an axis positioned by a distance L from the axis I in directions F. The upper mechanism 21 and the table 22 rotate with the elevator mechanism 23 when the bottom mechanism 24 is rotated by a predetermined angle.

For the radiotherapy practice, a medical staff such as a doctor D operates an operation unit (to be described in FIG. 13) connected to the controller 30 so as to position the patient P and determine the radiation field by the collimator 14.

In the radiotherapy practice, it is important to concentrate the radiation to a treated area or part such as a malignant tumor so as to avoid unnecessary X-ray exposure to normal tissues. The collimator 14 is used to control the radiation (field) to a limited area for the above purpose.

The collimator 14 will be described with reference to FIGS. 2 to 6. FIG. 2 is an illustration showing an exemplary configuration of the collimator 14 viewed from a first direction according to the first embodiment of the present invention. The collimator typically includes a first pair of collimating members 140A and 140B, and a second pair of collimating members 141A and 141B. The first pair may be perpendicular to the second pair. The first pair is placed at a first distance from an X-ray source S. The X-ray source S is part of the X-ray radiator. The second pair is placed at a second distance from the X-ray source S. The first distance may be shorter than the second distance.

The collimating members 140A and 140B may have, but are not limited to, an arc shape along a circular arc centered about the X-ray source S. The collimating members 140A and 140B may move along the circular arc (i.e., along direction X). The collimating members 140A and 140B may be opposed to each other and provided at symmetrical positions in relation to the axis I. The collimating member 140A may be a conventional aperture blade made of a heavy metal such as lead or tungsten, and move towards and away from the collimating member 140B. The collimating member 140A is driven by a driver 142A through a gear 144A. Similarly, the collimating member 140B may be a conventional aperture blade made of a heavy metal such as lead or tungsten, and move towards and away from the collimating member 140A. The collimating member 140B is driven by a driver 142B through a gear 144B. Therefore, the positions of the first pair of collimating members 140A and 140B are controlled so as to narrow or reduce the radiation field of the X-ray radiated from the X-ray source S in the direction X. Each of the collimating members 140A and 140B is independently controlled.

The positions of the second pair of collimating members 141A and 141B are controlled so as to further narrow or reduce the radiation field of the X-ray radiated from the X-ray source S in different directions. The collimating member 141A includes a plurality of collimating leaves 141A1 to 141An. Similarly, the collimating member 141B includes a plurality of collimating leaves 141B1 to 141Bn.

Figure 3:
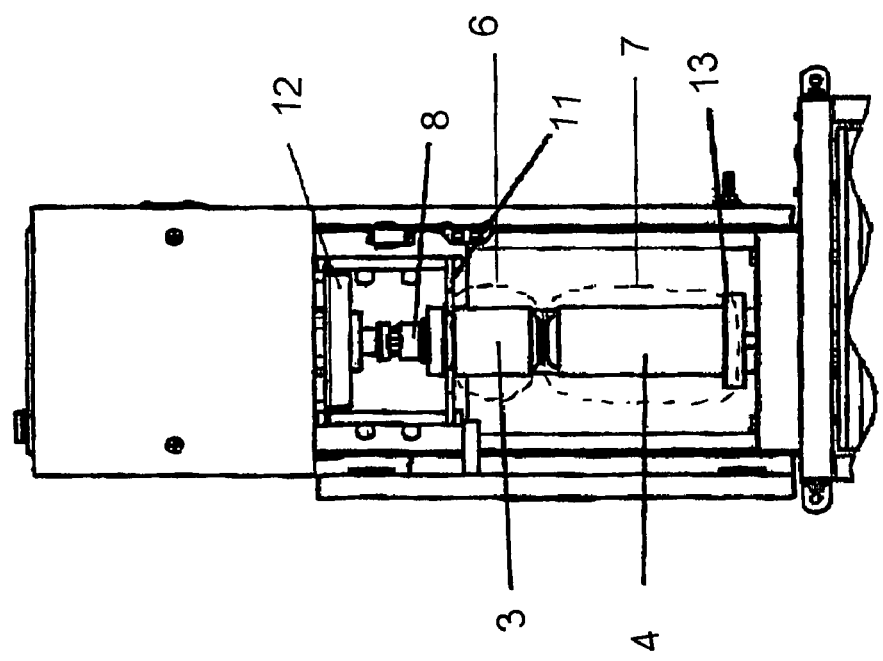
FIG. 3 is an illustration showing an exemplary configuration of the collimator viewed from a second direction according to the first embodiment of the present invention.

FIG. 3 is an illustration showing an exemplary configuration of the collimator 14 viewed from a second direction according to the first embodiment of the present invention. Since FIG. 3 shows a view from a direction perpendicular to the view shown in FIG. 2, FIG. 3 shows only one collimating leaf 141A1 as an example of the collimating member 141A. Similarly, only one collimating leaf 141B1 is shown as an example of the collimating member 141B. Therefore, the following explanation regarding the collimating leaf 141A1 also applies to collimating leaves 141A2 to 141An. The following explanation regarding the collimating leaf 141B1 also applies to collimating leaves 141B2 to 141Bn.

As shown in FIG. 3, the collimating leaves 141A1 and 141B1 may have, but are not limited to, an arc shape along a circular arc centered about the X-ray source S. The collimating leaves 141A1 and 141B1 may move along the circular arc (i.e., along directions Y). The collimating leaves 141A1 and 141B1 may be opposed to each other and be provided at symmetrical positions against the axis I. The collimating leaf 141A1 moves towards and away from the collimating leaf 141B1. The collimating leaf 141A1 is driven by a driver 143A1 through a driving gear 143a. Similarly, the collimating leaf 141B1 moves towards and away from the collimating leaf 141A1. The collimating leaf 141B1 is driven by a driver 143B1 through a driving gear 145B1. Therefore, the positions of the second pair of collimating members 141A and 141B are controlled so as to further narrow or reduce the radiation field in the directions Y, which has already been narrowed by the first pair of collimating members 140A and 140B. The position of each of the collimating leaves 141A1 and 141B1 are independently controlled. Further, the positions of each of the collimating leaves 141A1 to 141An are independently controlled and the positions of each of the collimating leaves 141B1 to 141Bn are also independently controlled. Therefore, as shown in FIG. 4, by controlling the position of each of the collimating leaves 141A1 to 141An and 141B1 to 141Bn, it is possible to adjust an aperture U to a shape of a malignant tumor T. The collimating leaves 141A1 to 141An and 141B1 to 141Bn will be described in detail below.

Figure 5:
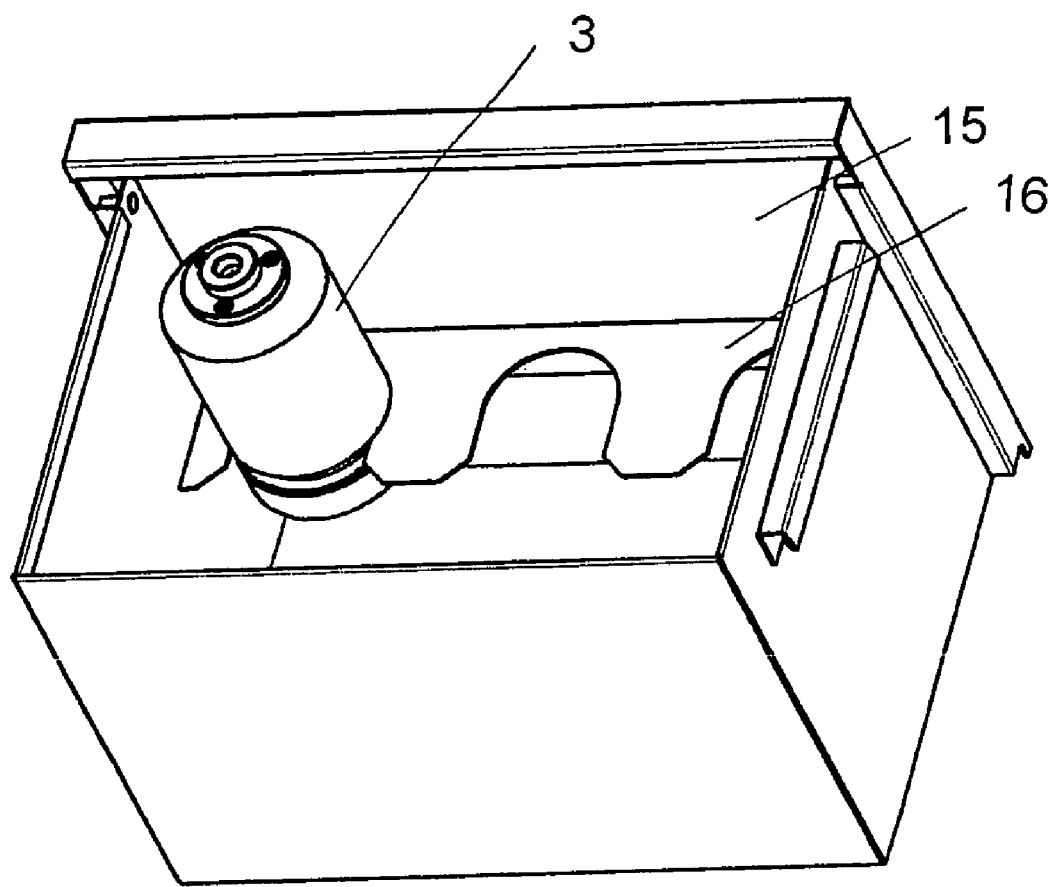
FIG. 5 is an illustration showing an exemplary configuration of the collimator viewed from a third direction according to the first embodiment of the present invention.

FIG. 5 is an illustration showing an exemplary configuration of the collimator 14 viewed from a third direction according to the first embodiment of the present invention. FIG. 5 shows a view from a top or a bottom of the collimator 14 along the axis I. The first pair of collimating members 140A and 140B is shown by chain double-dashed lines.

The collimating leaves 141A1 to 141An are arranged in a mutually contiguous manner. As the collimating leaf 141A1 has been described as connected to the driver 143A1, the collimating leaves 141A1 to 141An are connected to drivers 143A1 to 143An, respectively. Accordingly, the collimating leaves 141A1 to 141An are independently driven by the drivers 143A1 to 143An, respectively. Similarly, the collimating leaves 141B1 to 141Bn are arranged in a mutually contiguous manner. As the collimating leaf 141B1 has been described as connected to the driver 143B1, the collimating leaves 141B1 to 141Bn are connected to drivers 143B1 to 143Bn, respectively. Accordingly, the collimating leaves 141B1 to 141Bn are independently driven by the drivers 143B1 to 143Bn, respectively.

Figure 6:
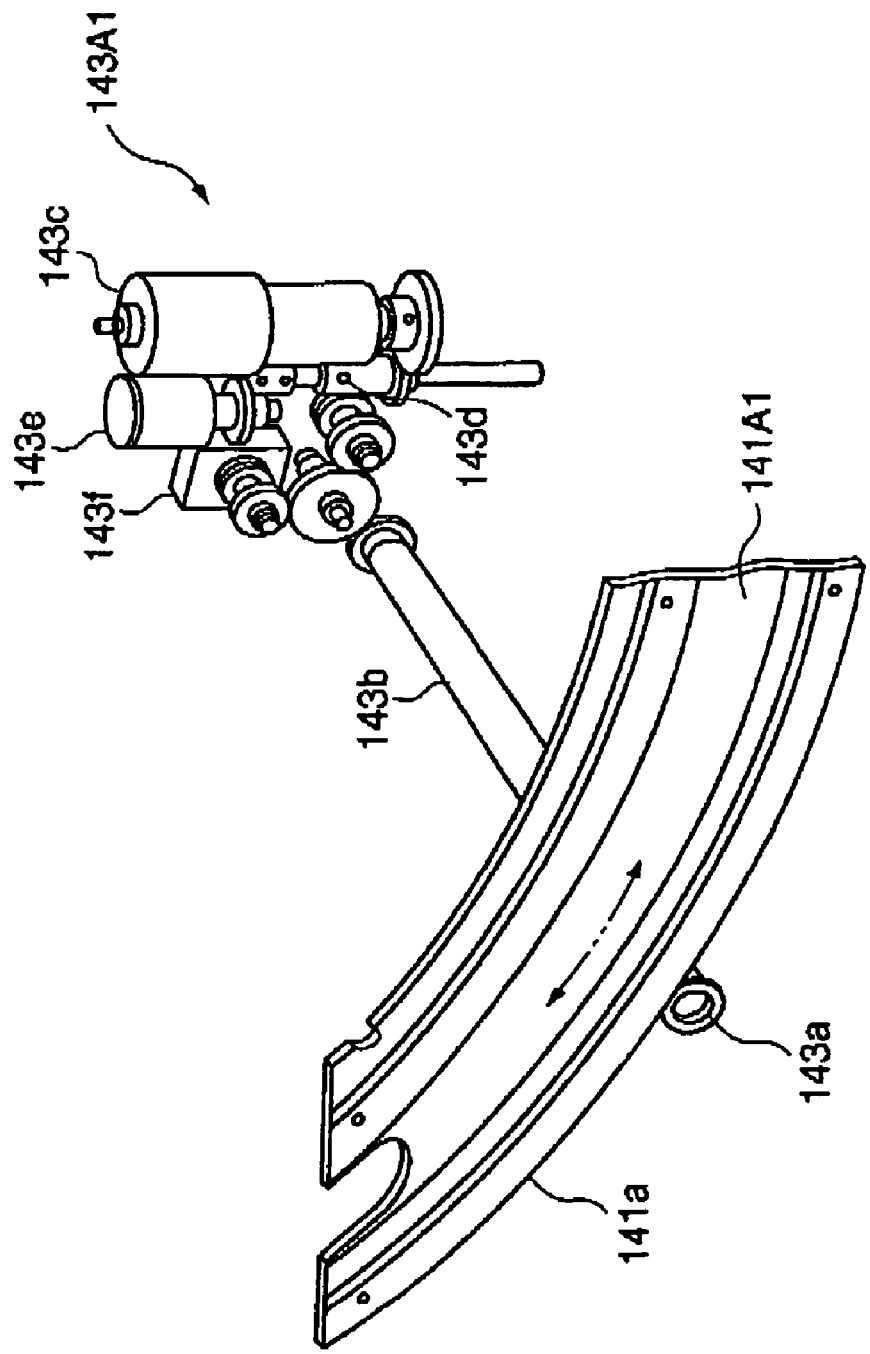
FIG. 6 is an illustration showing an example of a driver according to the first embodiment of the present invention.

FIG. 6 is an illustration showing an example of the driver 143A1 according to the first embodiment of the present invention. The following explanation of the driver 143A1 also applies to the drivers 143A2 to 143An and 143B1 to 143Bn. FIG. 6 shows a relationship between the driver 143A1 and the collimating leaf 141A1. As shown in FIG. 6, the collimating leaf 141A1 is formed of a sector with an arc along a bottom edge 141a. The side far from the collimating leaf 141B1 (not shown in FIG. 6) is formed of a wedge. This side may alternatively be flat. The other side of the collimating leaf 141A1 by which the radiation is collimated is flat. The bottom edge 141a has gear teeth so as to engage with the driving gear 143a. The driving gear 143a is fixed at one end of a shaft 143b. The shaft 143b is driven by a motor 143c through a warm gear 143d and the other gears. Accordingly, the shaft 143b rotates in accordance with the motor 143c. The driver 143A1 also includes a potentiometer 143e and an encoder 143f. The potentiometer 143e and the encoder 143f are used to detect position information of the collimating leaf 141A1. Outputs of the potentiometer 143e and the encoder 143f are supplied to the controller 30. The controller 30 controls the motor 143c based on the supplied outputs, allowing the collimating leaf 141A1 to be positioned appropriately.

Next, a control technique of the collimator 14 will be described below.

Regarding the first pair of collimating members 140A and 140B, the collimating member 140A is moved away from the collimating member 140B along the direction X. There is a stopper (or a holder) to hold the collimating member 140A at a position furthest from the collimating member 140B. A position control determination of the collimating member 140A is performed based on the held position. Similarly, the collimating member 140B is moved away from the collimating member 140A along the direction X. There is a stopper (or a holder) to hold the collimating member 140B at a position furthest from the collimating member 140A. A position control determination of the collimating member 140B is performed based on the held position. The controller 30 controls the drivers 142A and 142B so as to move the collimating members 140A and 140B to appropriate positions. Accordingly, the collimator 14 adjusts its aperture with a preferred width along the X direction. The relationship between the collimating member 140A (140B) and the driver 142A (142B) is similar to that between the collimating leaf 141A1 and the driver 143A1.

Regarding the second pair of collimating members 141A and 141B, it is necessary to accurately control the position of each collimating leaf along the Y direction so as to obtain a preferred radiation field through the aperture of the collimator 14. Although there is a technique of positioning each collimating leaf in a manner similar to the first pair of the collimating members 140A and 140B, it is not preferable since each collimating leaf may be transformed due to an impact shock caused when the collimating leaf is held by the stopper.

Therefore, according to the first embodiment of the present invention, a reference position (or position information) of each collimating leaf is accurately determined without any impact shock to each collimating leaf. Accordingly, the position of each collimating leaf of the collimating leaves 141A1 to 141An and 141B1 to 141Bn is controlled based on the position information so as to obtain a desired aperture (or a desired radiation field on the patient P). In other words, the controller 30 controls the distance each collimating leaf is moved based on the position information. As shown in FIG. 5, the collimator 14 includes a laser beam generator 41 and a laser beam receiver 42 so as to determine the reference position. The laser beam receiver 42 includes a function as a detector for detecting a received laser beam.

The laser beam generator 41 and the laser beam receiver 42 are opposed to each other so that a laser beam 40 generated from the laser beam generator 41 emanates between the collimating members 141A and 141B. The laser beam 40 also intersects the axis I. One example is that the laser beam 40 runs in a direction perpendicular to the direction Y. In other words, an incident angle of the laser beam 40 between the collimating members 141A and 141B is 90 degrees in relation to the direction Y. Another example is that the laser beam direction may not be perpendicular to the direction Y. The incident angle is, for example, 85 degrees in relation to the direction Y. In another example above, position information of each collimating leaf is compensated based on the incident angle and a position along the direction X in the collimating member 141A or 141B. The compensated position information is used as the reference position.

Figure 7:
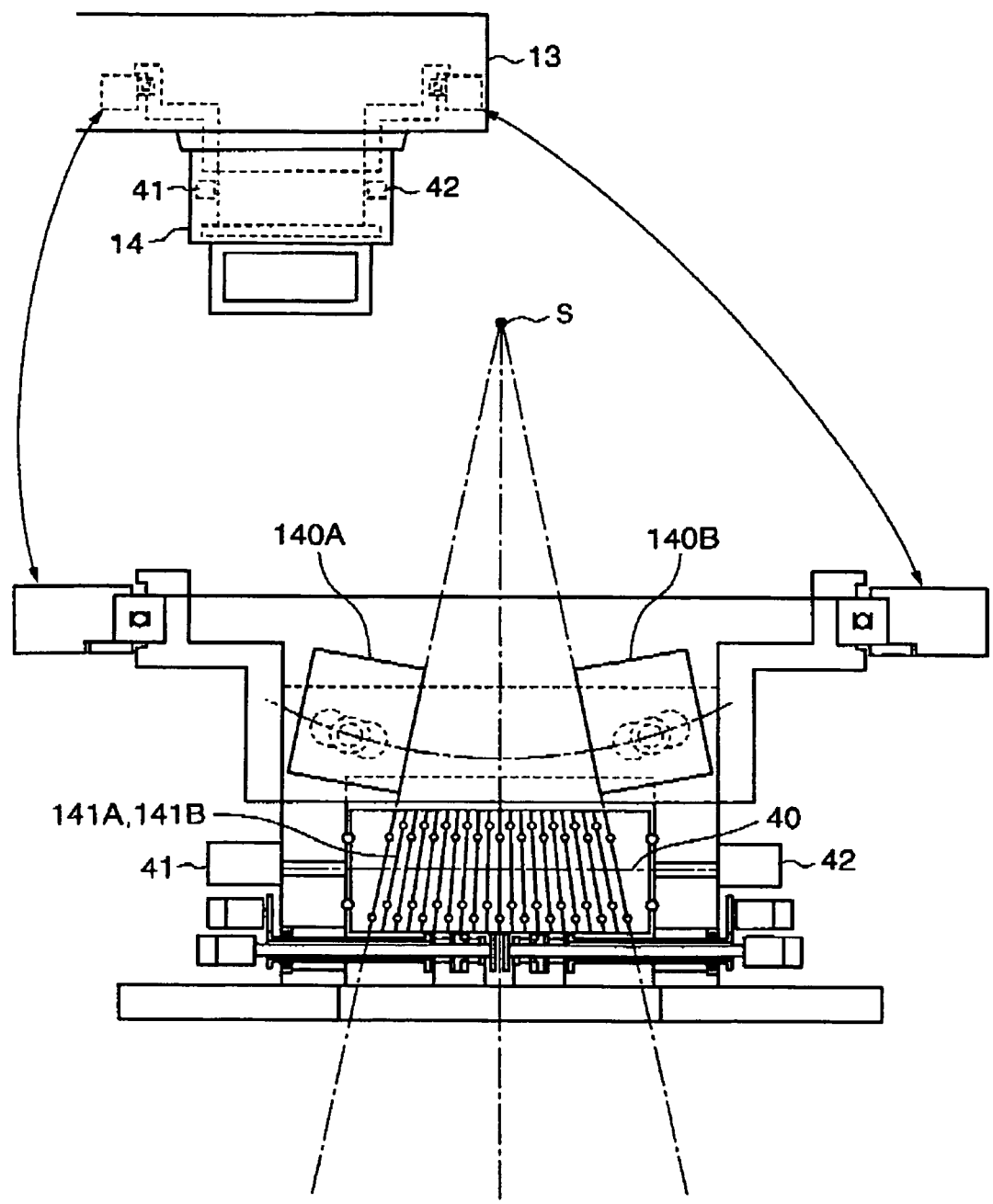
FIG. 7 is an illustration showing exemplary positions of a laser beam generator and a laser beam receiver in the collimator according to the first embodiment of the present invention.

The laser beam generator 41 and the laser beam receiver 42 are placed, for example, at positions shown in FIG. 7 as part of the collimator 14. The collimator 14 is supported in the radiation head 13.

Prior to the laser beam generation, the collimating leaves 141A1 to 141An are moved away from the collimating leaves 141B1 to 141Bn along the direction Y. There are stoppers (or holders) to hold the collimating leaves 141A1 to 141An at positions furthest from the collimating leaves 141B1 to 141Bn. Similarly, the collimating leaves 141B1 to 141Bn are moved away from the collimating leaves 141A1 to 141An along the direction Y. There are stoppers (or holders) to hold the collimating leaves 141B1 to 141Bn at positions furthest from the collimating leaves 141B1 to 141Bn.

After the holding of the collimating leaves 141A1 to 141An and 141B1 to 141Bn, each collimating leaf is individually moved towards the laser beam 40. For example, the collimating leaf 141A1 is moved towards the laser beam 40 (i.e., towards the collimating leaf 141B1). When the collimating leaf 141A1 intersects the laser beam 40 at the first position, the first position is detected by the potentiometer 143e or the encoder 143f as the reference position of the collimating leaf 141A1. The detected reference position is stored as the position information of the collimating leaf 141A1 in a memory of the controller 30. After the detection regarding the collimating leaf 141A1, the collimating leaf 141A1 is moved back to the position of the stopper. In response, the collimating leaf 141A2 is moved towards the laser beam 40 (i.e., towards the collimating leaf 141B2)1. When the collimating leaf 141A2 intersects the laser beam 40 at the second position, the second position is detected by the potentiometer 143e or the encoder 143f as the reference position of the collimating leaf 141A2. The detected reference position is stored as the position information of the collimating leaf 141A2 in a memory of the controller 30. A similar detection is repeated for the rest of the collimating leaves (i.e., the collimating leaves 141A3 to 141An and 141B1 to 141Bn).

Figure 8:
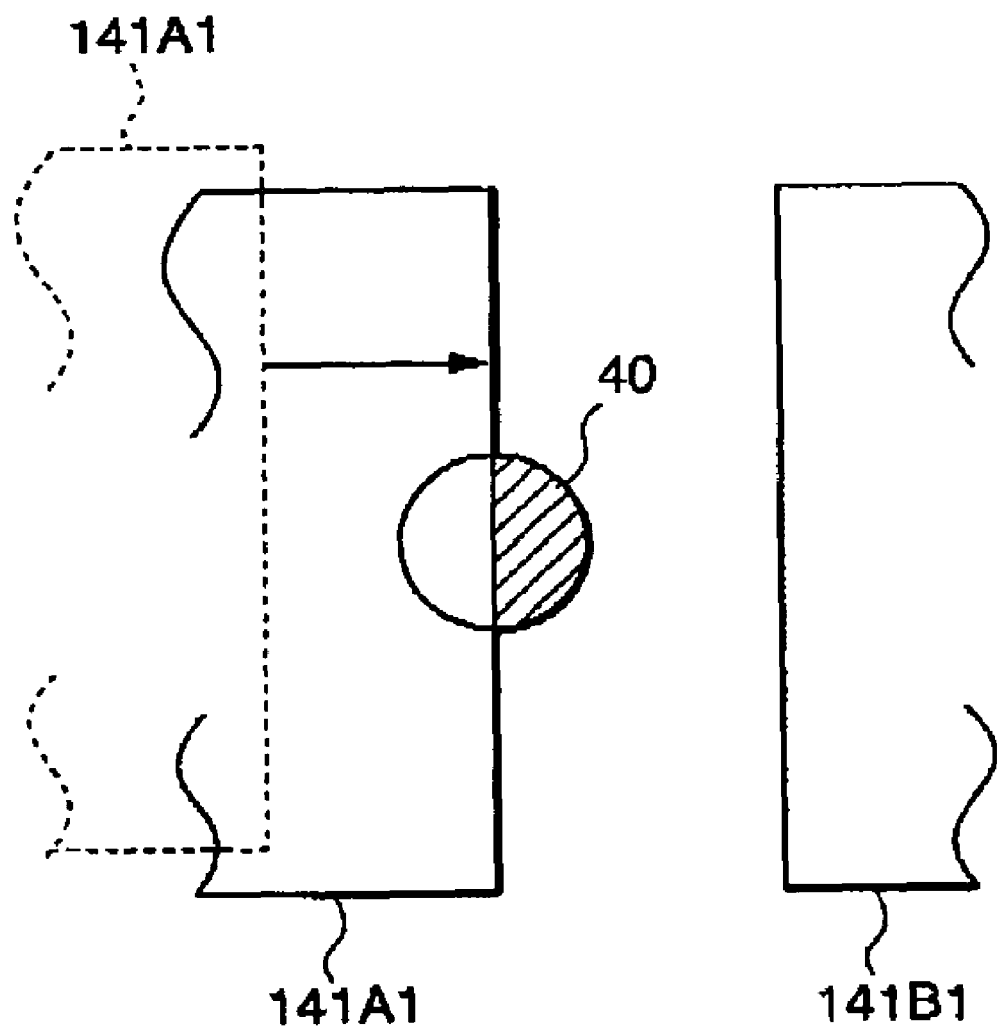
FIG. 8 is an illustration showing an example of an intersection between a collimating leaf and a laser beam according to the first embodiment of the present invention.

In the above case, the intersection may be determined when the laser beam receiver 42 detects the received laser beam 40 at a predetermined percentage which can be detected without any intersection of the collimating leaf 141A1, as shown in FIG. 8. For example, the predetermined percentage may be 50 percent. As a modification, the collimating leaf may first be moved to a position where the laser beam is completely blocked, and then moved back to a position where the laser beam is half blocked.

Figure 9:
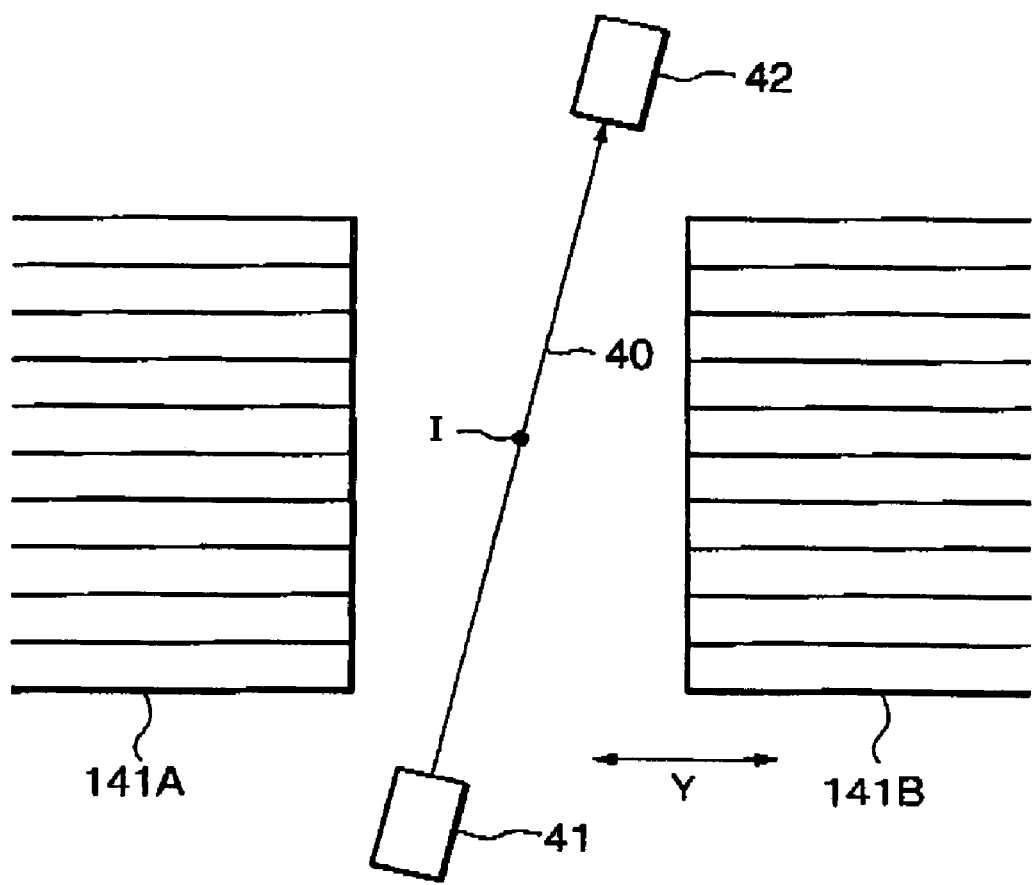
FIG. 9 is an illustration showing an example of an incident angle of the laser beam according to the first embodiment of the present invention.

As described above, when the laser beam 40 does not emanate between the collimating members 141A and 141B in a direction perpendicular to the direction Y as shown in FIG. 9, the detected reference position (position information) maybe compensated in accordance with the incident angle of the laser beam 40.

Figure 10:
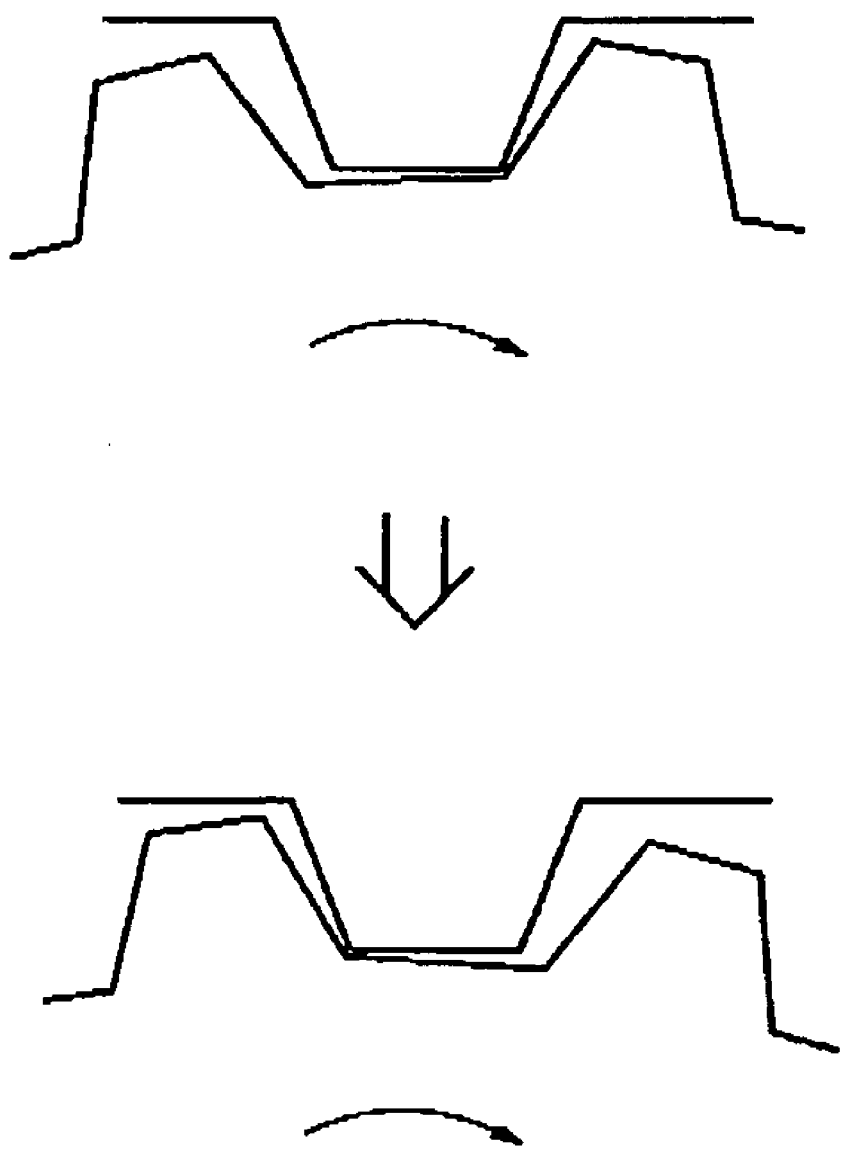
FIG. 10 is an illustration showing an example of a gear engagement according to the first embodiment of the present invention.

Further, as shown in FIG. 10, when a gear mechanism is used to move a collimating leaf, the relationship between positions of the collimating leaf and the shaft 143b is changed due to a gear engagement in the gear rotation. Therefore, the reference position may also be compensated in accordance with a rotation direction of the shaft 143b (i.e., a moving direction of the collimating leaf), taking the gear engagement into consideration. In this case, for example, two types of compensated position information may be prepared, one for a first direction (e.g., left) and one for a second direction (e.g., right). This compensation may also take a rotation amount or angle of the shaft into consideration since the above relationship between positions of the collimating leaf and the shaft 143b is kept until the shaft 143b is rotated by a certain angle. Similar compensation may also be applied to a rotation of the rotation gantry 12. In other words, the position information may be compensated in accordance with the rotation angle of the rotation gantry 12 and the compensated position information may be used to position the collimating leaves 141A1 to 141An and 141B1 to 141Bn in accordance with a rotation angle used in a radiotherapy.

Figure 11:
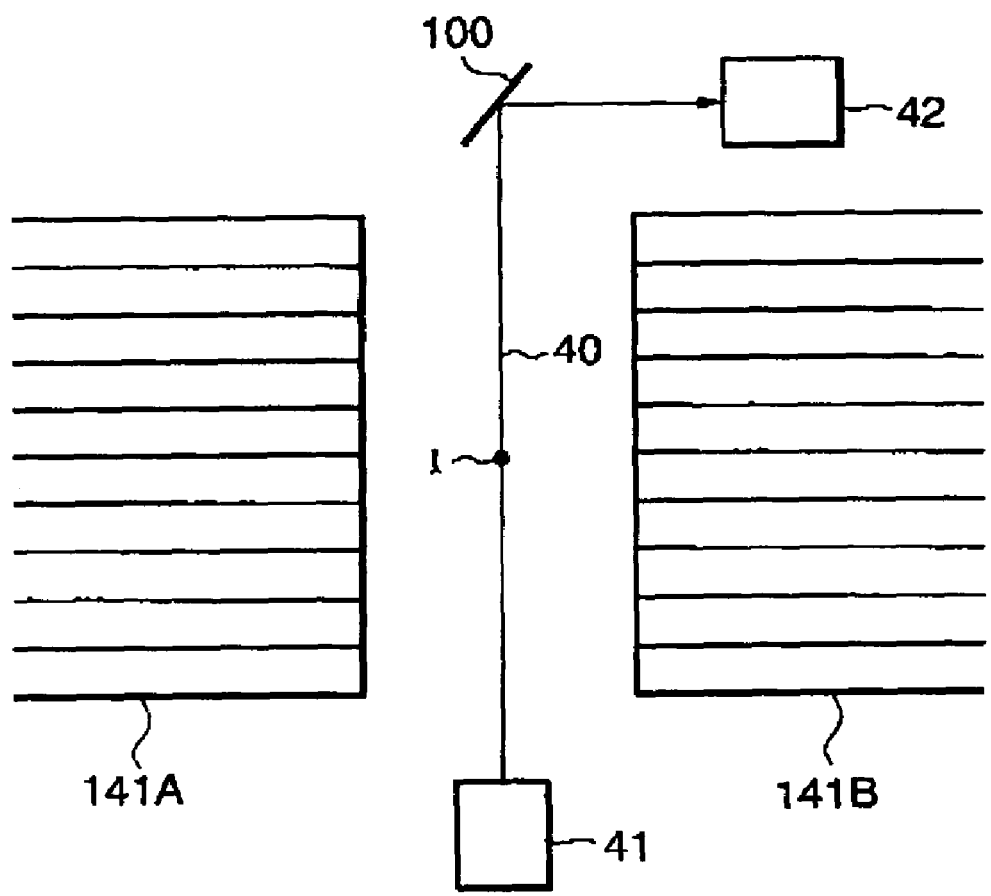
FIG. 11 is an illustration showing the first example of laser beam reflection by a reflector according to the first embodiment of the present invention.
Figure 12:
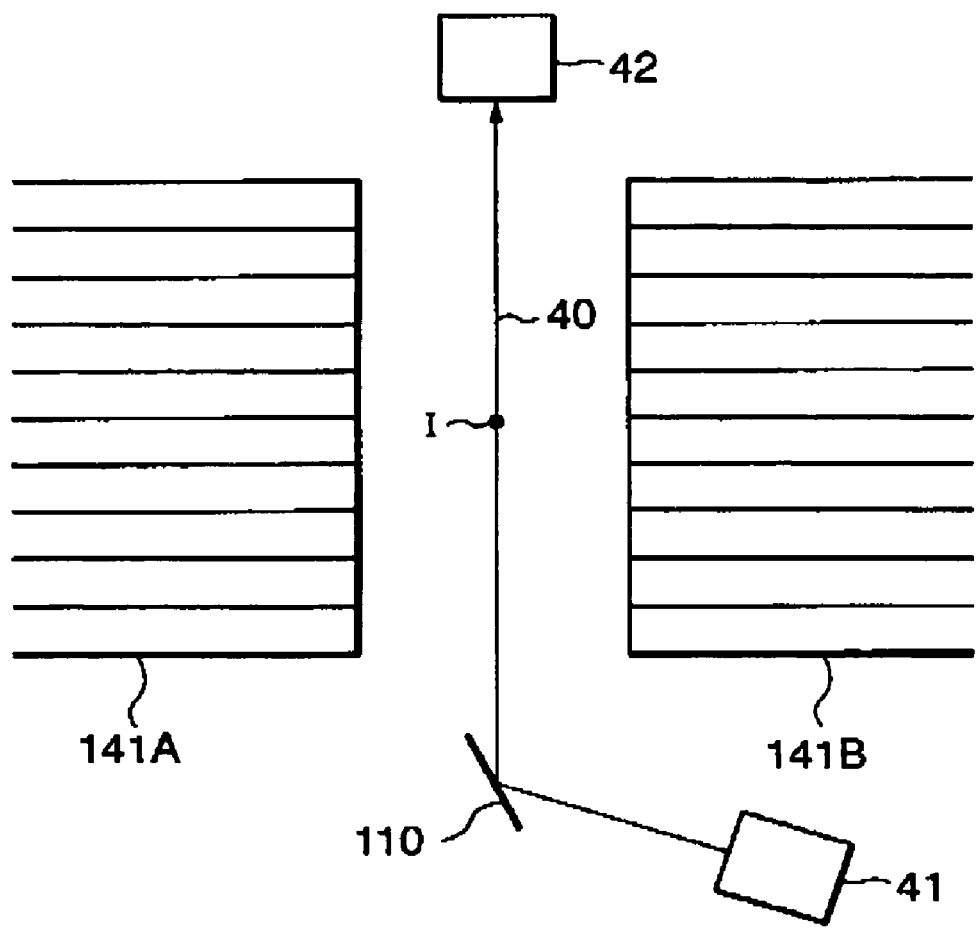
FIG. 12 is an illustration showing the second example of the laser beam reflection by a reflector according to the first embodiment of the present invention.

The laser beam 40 generated by the laser beam generator 41 is not necessarily received by the laser beam receiver 42 directly. As shown in FIG. 11, after having passed through the collimating members 141A and 141B, the laser beam 40 generated by the laser beam generator 41 may be reflected by one or more mirrors 100 (reflectors), and then be received by the laser beam receiver 42. Another example is shown in FIG. 12. The laser beam 40 generated by the laser beam generator 41 may be reflected by one or more mirrors 110 (reflectors) before passing through the collimating members 141A and 141B, and then be received by the laser beam receiver 42.

Instead of the laser beam generator 41 and the laser beam receiver 42, a photo-sensing system may be used for the same purpose.

Figure 13:
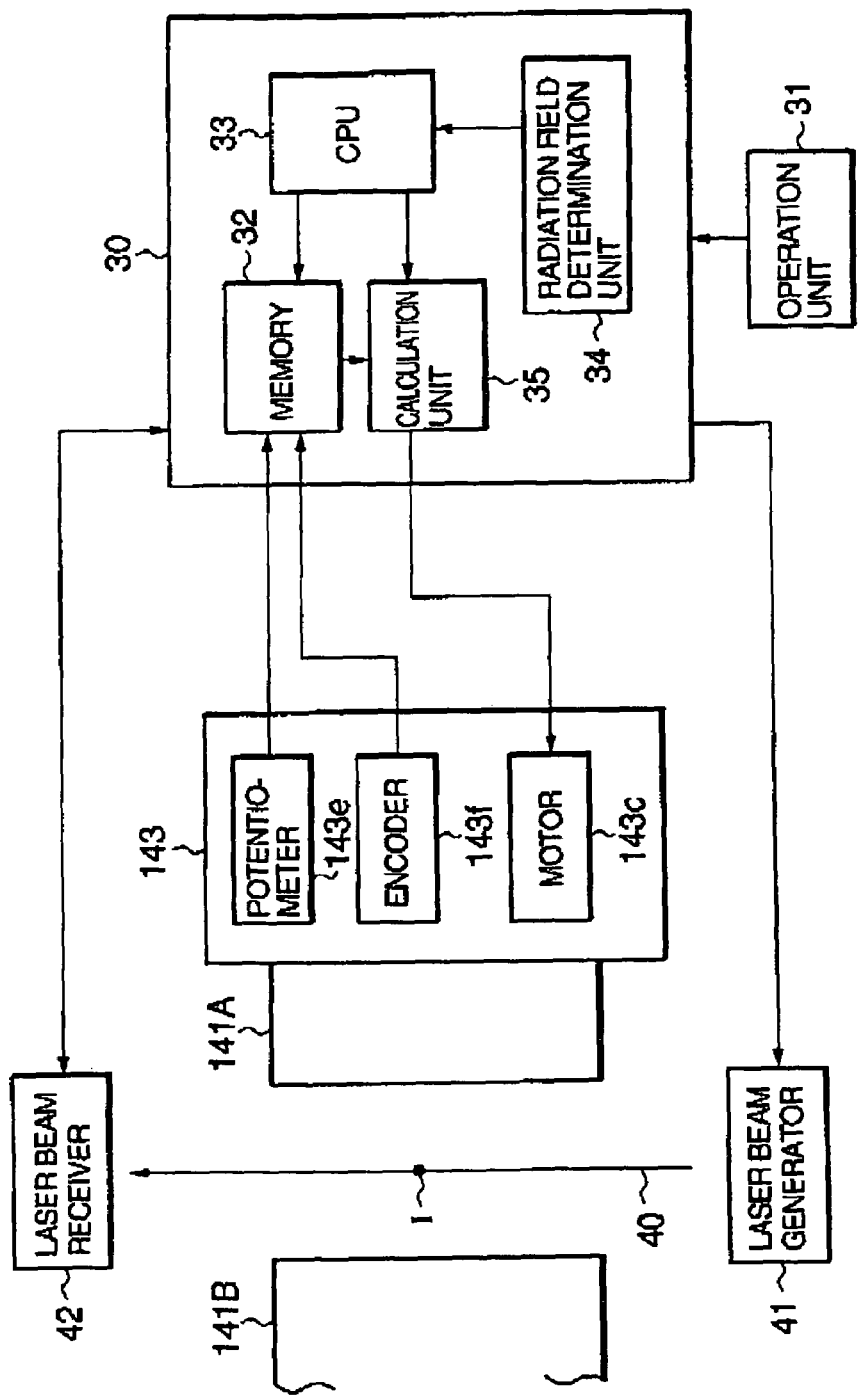
FIG. 13 is a block diagram showing an exemplary configuration regarding a collimator control according to the first embodiment of the present invention.
Figure 14:
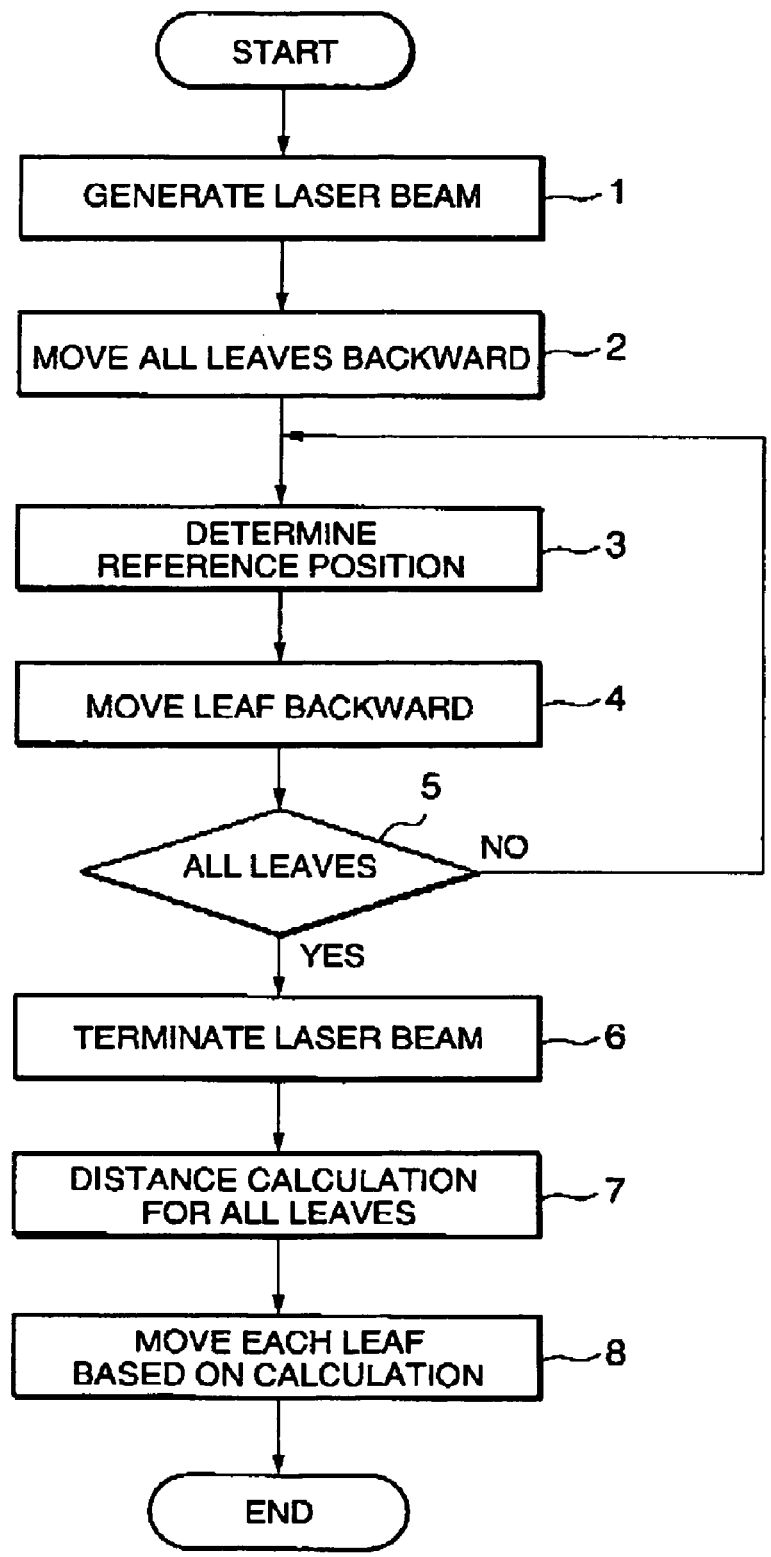
FIG. 14 is a flowchart showing an example of a flow of reference position determination and collimating leaf positioning according to the first embodiment of the present invention.

Basic operations of determining the reference position of each collimating leaf and positioning each collimating leaf will be described with reference to FIGS. 12 and 13. FIG. 13 is a block diagram showing an exemplary configuration of a collimator control apparatus according to the first embodiment of the present invention. FIG. 14 is a flowchart showing an example of a flow of the reference position determination and the collimating leaf positioning according to the first embodiment of the present invention.

As shown in FIG. 13, the controller 30 controls various components of the radiotherapy apparatus and is connected to an operation unit 31. The operation unit 31 is used to input various types of information and to instruct various operations. The controller 30 includes a memory 32, a central processing unit (CPU) 33, a radiation field determination unit 34, and a calculation unit 35. The memory 32 stores the position information as described above. The CPU 33 operates as a host controller. The radiation field determination unit 34 determines an aperture of the collimator 14 so as to control the radiation field of an X-ray radiated by the X-ray source S. The calculation unit 35 calculates a movement distance of the collimating leaves 141A1 to 141An and 141B1 to 141Bn. The controller 30 also calculates a movement distance of the collimating members 140A and 140B. The controller 30 further includes one or more processors for controls of, for example, a radiation, the rotation gantry 12, and the patient couch 20. Since, however, these processors do not directly relate to explanations of the collimator 14 according to the first embodiment, explanations of these controls are omitted herein.

The doctor D operates the operation unit 31 so as to instruct the reference position determination for each collimating leaf of the collimating members 141A and 141B. In response to the instruction, the CPU 33 activates (or renders operative) the laser beam generator 41 and the laser beam receiver 42 so that the laser beam is generated (step 1). The CPU 33 also drives the motor 143c so as to move all the collimating leaves 141A1 to 141An and 141B1 to 141Bn backward (step 2). That is, the collimating leaves 141A1 to 141An are moved away from the collimating leaves 141B1 to 141Bn and held by the stoppers. Also, the collimating leaves 141B1 to 141Bn are moved away from the collimating leaves 141A1 to 141An and held by the stoppers. The processing order of steps 1 and 2 may also be reversed. An operator who operates the operation unit 31 so as to instruct the reference position determination is not limited to the doctor D but may be any other permitted person.

The collimating leaf 141A1 is moved from the position held by the stopper towards the collimating leaf 141B1. The collimating leaf 141A1 is stopped at a position where the collimating leaf 141A1 intersects the laser beam 40. For example, the received laser beam may be 50 percent in strength of the laser beam received without any intersection. The position is detected by the potentiometer 143e or the encoder 143f as a reference position of the collimating leaf 141A1. The detected reference position is stored as position information of the collimating leaf 141A1 in the memory 32 (step 3). After the detection and the storage, the collimating leaf 141A1 is moved back to the position of the stopper (step 4). In step 5, it is determined whether reference positions are detected for all the collimating leaves 141A1 to 141An and 141B1 to 141Bn. Therefore, the operations in steps 3 and 4 are performed individually for each of the collimating leaves 141A1 to 141An and 141B1 to 141Bn. When the reference position is detected and stored as position information for each of the collimating leaves 141A1 to 141An and 141B1 to 141Bn, the operation of the laser beam generator 41 and the laser beam receiver 42 are terminated (step 6).

The calculation unit 35 then calculates a distance of how much each of the collimating leaves 141A1 to 141An and 141B1 to 141Bn should be moved so as to form an aperture corresponding to a radiation field designated for a particular radiotherapy (step 7). The calculated distance is a distance from the reference position. Based on the calculated distance for each of the collimating leaves 141A1 to 141An and 141B1 to 141Bn, each collimating leaf is positioned by driving the motor 143c (step 8). In addition, the calculation unit 30 also calculates the distance to move each of the collimating members 140A and 140B to form the designated radiation field.

Accordingly, all the collimating leaves 141A1 to 141An of the collimating member 141A and 141B1 to 141Bn of the collimating member 141B and the collimating members 140A and 140B are positioned, respectively, to form the aperture corresponding to the radiation field appropriate for the shape of a tumor.

The operations in steps 1 to 6 are not limited to being performed just prior to an actual radiotherapy. The operations may, for example, be performed any time the radiotherapy apparatus is powered. In other words, the laser beam generator 41 can be activated in response to the power supply to the radiotherapy apparatus without the doctor D's instruction. Also, the operations may alternatively be performed at predetermined intervals, for example, every three months or during other predetermined intervals. These calibrations are effective to correct deviance that might occur due to the use of the device (or the several times of use). The operations in steps 1 to 6 may, for example, take only three minutes.

The position information (the reference position) and/or the calculated distance may be displayed in a display provided in or connected to the radiotherapy apparatus.

As explained above, according to the first embodiment of the present invention, the reference position (position information) of each collimating leaf is accurately determined without any impact shock to each collimating leaf. Accordingly, the position of each collimating leaf of the collimating leaves 141A1 to 141An and 141B1 to 141Bn is controlled based on the position information. This makes it possible to easily and accurately obtain a desired aperture corresponding to the radiation field which is appropriate for the shape of a tumor. In addition, since the reference position of each collimating leaf can automatically be detected, it is possible to accurately and quickly adjust positioning of a plurality of collimating leaves. Therefore, the X-ray exposure to the patient P can be highly reduced, and a preferred radiotherapy can be conducted to the patient P. A medical staff's work can also be reduced.

(Second Embodiment)

The first embodiment has described the collimating leaf position detection with one laser beam. In the second embodiment, various types of collimating leaf position detections using a plurality of laser beams will be described with reference to FIGS. 14 to 22.

Figure 15:
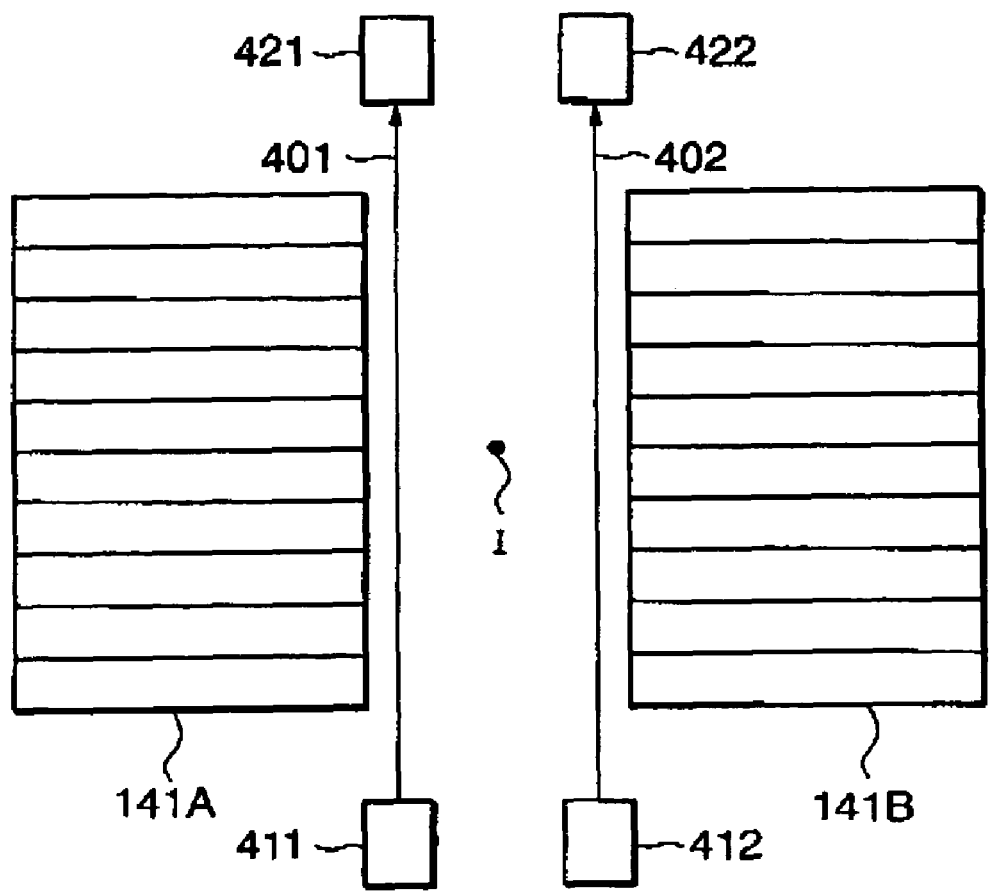
FIG. 15 is an illustration showing the first example of collimating leaf position detection with two laser beams according to the second embodiment of the present invention.

FIG. 15 is an illustration showing the first example of the collimating leaf position detection with two laser beams according to the second embodiment of the present invention. As shown in FIG. 15, a laser beam 401 generated from a laser beam generator 411 is received by a laser beam receiver 421. The laser beam 401 may be used to detect a position of each collimating leaf of the collimating member 141A. Similarly, the laser beam 402 generated from a laser beam generator 412 is received by a laser beam receiver 422. The laser beam 402 may be used to detect a position of each collimating leaf of the collimating member 141B. In this configuration, it may be possible to perform the detection for both of the collimating members 141A and 141B at the same time.

Figure 16:
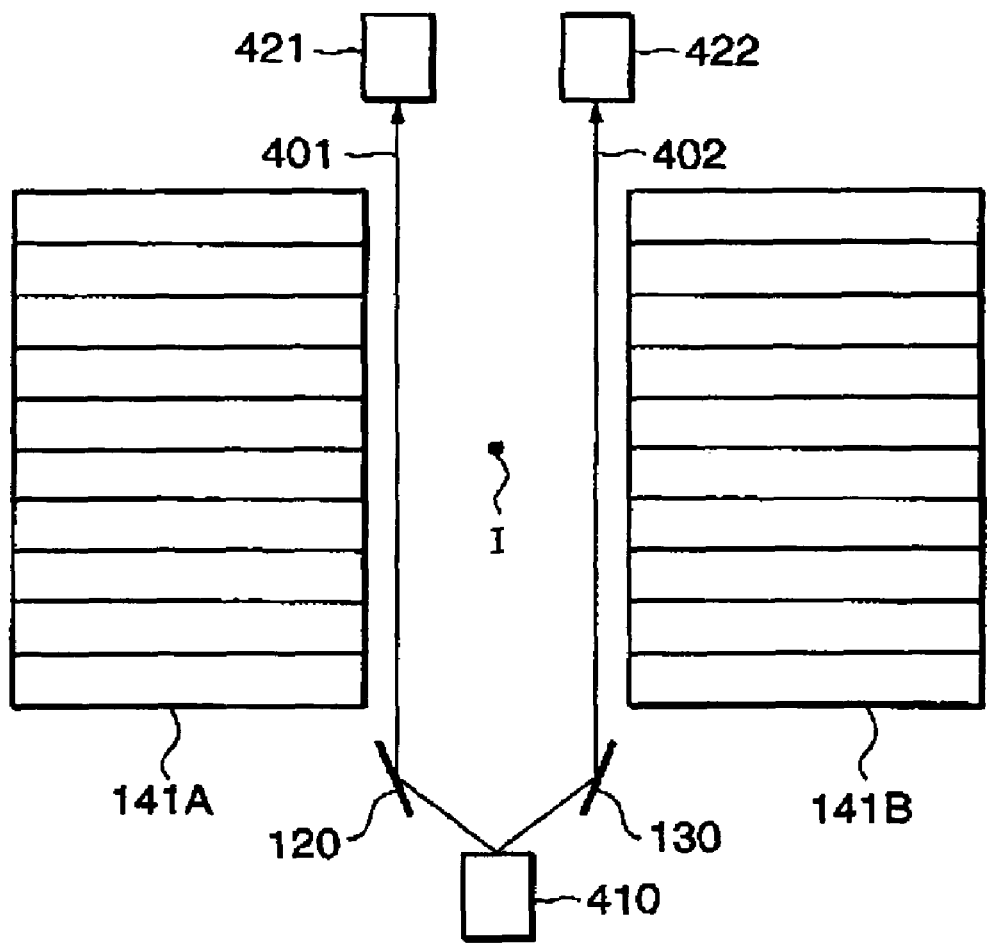
FIG. 16 is an illustration showing the second example of the collimating leaf position detection with two laser beams according to the second embodiment of the present invention.

FIG. 16 is an illustration showing the second example of the collimating leaf position detection with two laser beams according to the second embodiment of the present invention. As shown in FIG. 16, both the laser beams 401 and 402 are generated from a laser beam generator 410. The laser beam 401 is reflected by a mirror 120 or any other type of reflector and received by the laser beam receiver 421. The laser beam 402 is reflected by a mirror 130 or any other type of reflector and received by the laser beam receiver 422. Similarly to FIG. 15, the laser beam 401 reflected by the mirror 120 may be used to detect a position of each collimating leaf of the collimating member 141A. The laser beam 402 reflected by the mirror 130 may be used to detect a position of each collimating leaf of the collimating member 141B. If the laser beam generator 410 is capable of generating the laser beam 402 while the laser beam 401 is generated, it may be possible to perform the detection for both of the collimating members 141A and 141B at the same time.

According to the configuration shown in FIG. 16, only one laser beam generator is required for the detection with two laser beams. The placement relationship among the laser beam generator 410 and the mirrors 120 and 130 can be arranged according to necessity. Instead of the use of only one laser beam generator 410, only one laser beam receiver may be used with reflectors such as mirrors. Or alternatively, only one laser beam generator may be used with only one laser beam receiver for two laser beams, using reflectors at both ends.

Figure 17:
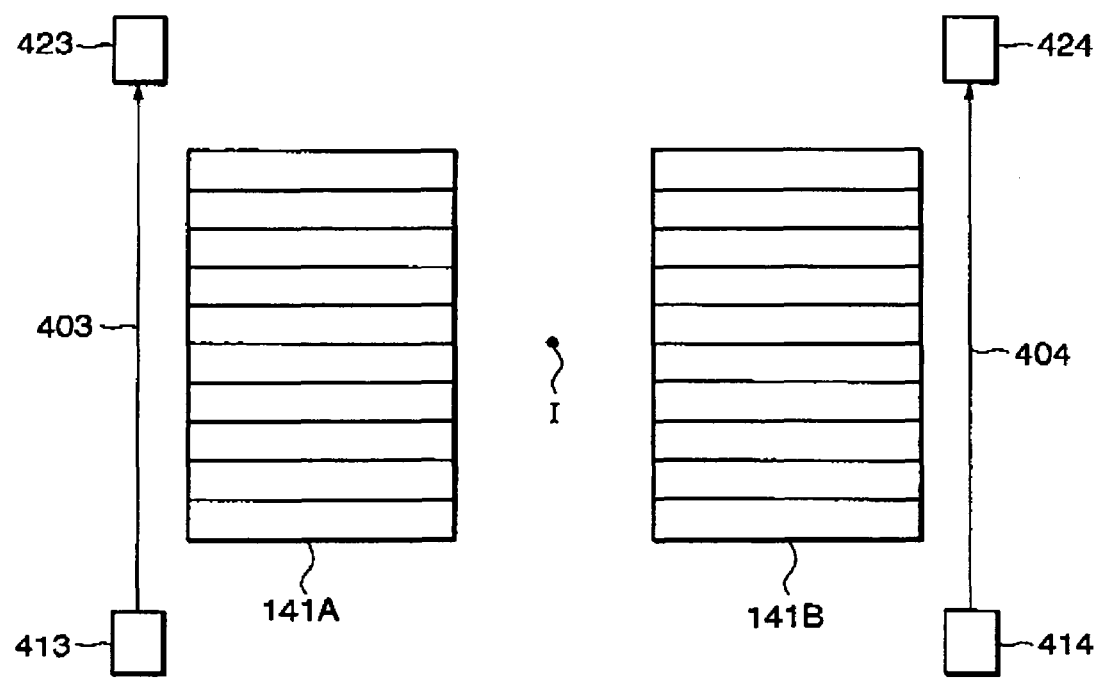
FIG. 17 is an illustration showing the third example of the collimating leaf position detection with two laser beams according to the second embodiment of the present invention.

FIG. 17 is an illustration showing the third example of the collimating leaf position detection with two laser beams according to the second embodiment of the present invention. As shown in FIG. 17, a laser beam 403 generated from a laser beam generator 413 is received by a laser beam receiver 423. The laser beam 403 may be used to detect a position of each collimating leaf of the collimating member 141A. In this example, the side furthest from the collimating member 141B intersects the laser beam 403. Similarly, the laser beam 404 generated from a laser beam generator 414 is received by a laser beam receiver 424. The laser beam 404 may be used to detect a position of each collimating leaf of the collimating member 141B. The side furthest from the collimating member 141A intersects the laser beam 404. Also in this configuration, it may be possible to perform the detection for both of the collimating members 141A and 141B at the same time.

Figure 18:
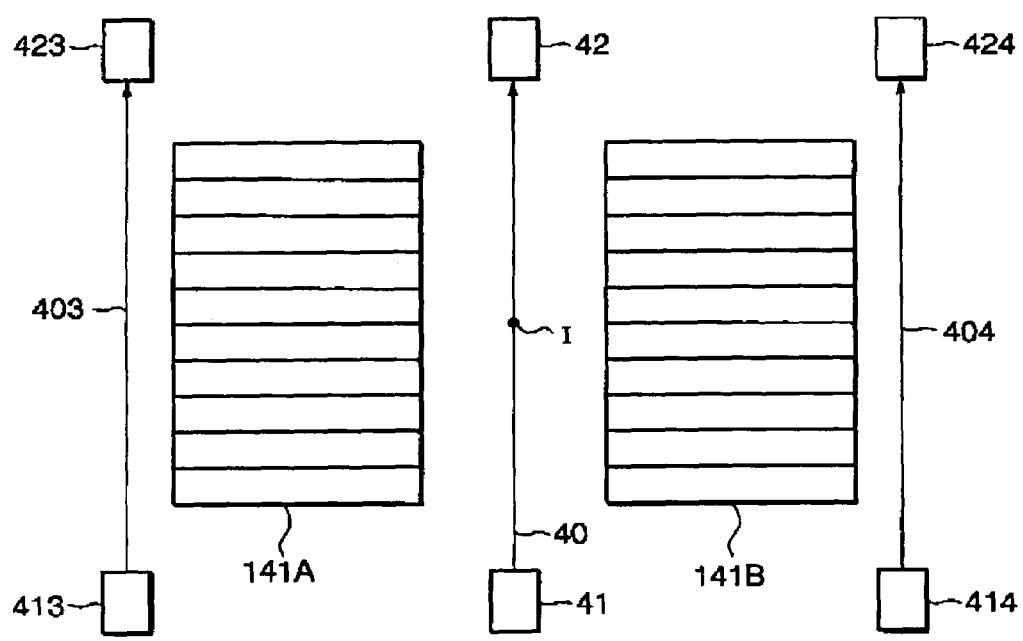
FIG. 18 is an illustration showing an example of the collimating leaf position detection with three laser beams according to the second embodiment of the present invention.
Figure 19:
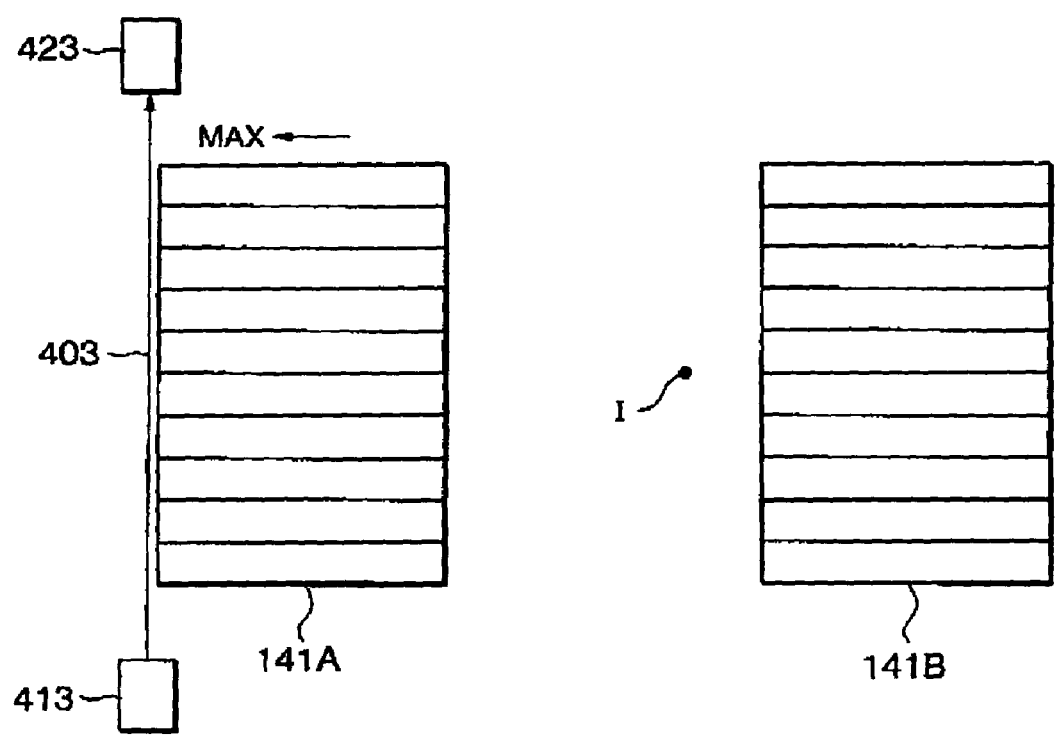
FIG. 19 is an illustration showing the first aspect of the collimating leaf position detection shown in FIG. 18 according to the second embodiment of the present invention.

FIG. 18 is an illustration showing an example of the collimating leaf position detection with three laser beams according to the second embodiment of the present invention. As shown in FIG. 18, the laser beams 40, 403, and 404 are generated from respective laser beam generators 41, 413, and 414. The generated laser beams 40, 403, and 404 are received by the respective laser beam receivers 42, 421, and 424. As shown in FIG. 19, a pair of the laser beam generator 413 and the laser beam receiver 423 is placed where the laser beam 403 intersects the side of the collimating member 141A furthest from the collimating member 141B when the collimating member 141A is moved furthest from the collimating member 141B. Position information detected at this position may be used when the collimating leaf of the collimating member 141A is moved and positioned against the collimating member 141B. Similarly, although not shown in FIG. 19, the laser beam generator 414 and the laser beam receiver 424 pair is placed where the laser beam 404 intersects one side of the collimating member 141B which is further from the collimating member 141A when the collimating member 141B is moved furthest from the collimating member 141A. Position information detected at this position regarding each collimating leaf may be used when the collimating leaf of the collimating member 141B is moved against the collimating member 141A. Such a use of position information may be advantageous when the gear engagement is changed in accordance with the moving direction of each collimating leaf, as shown in FIG. 10.

Figure 20:
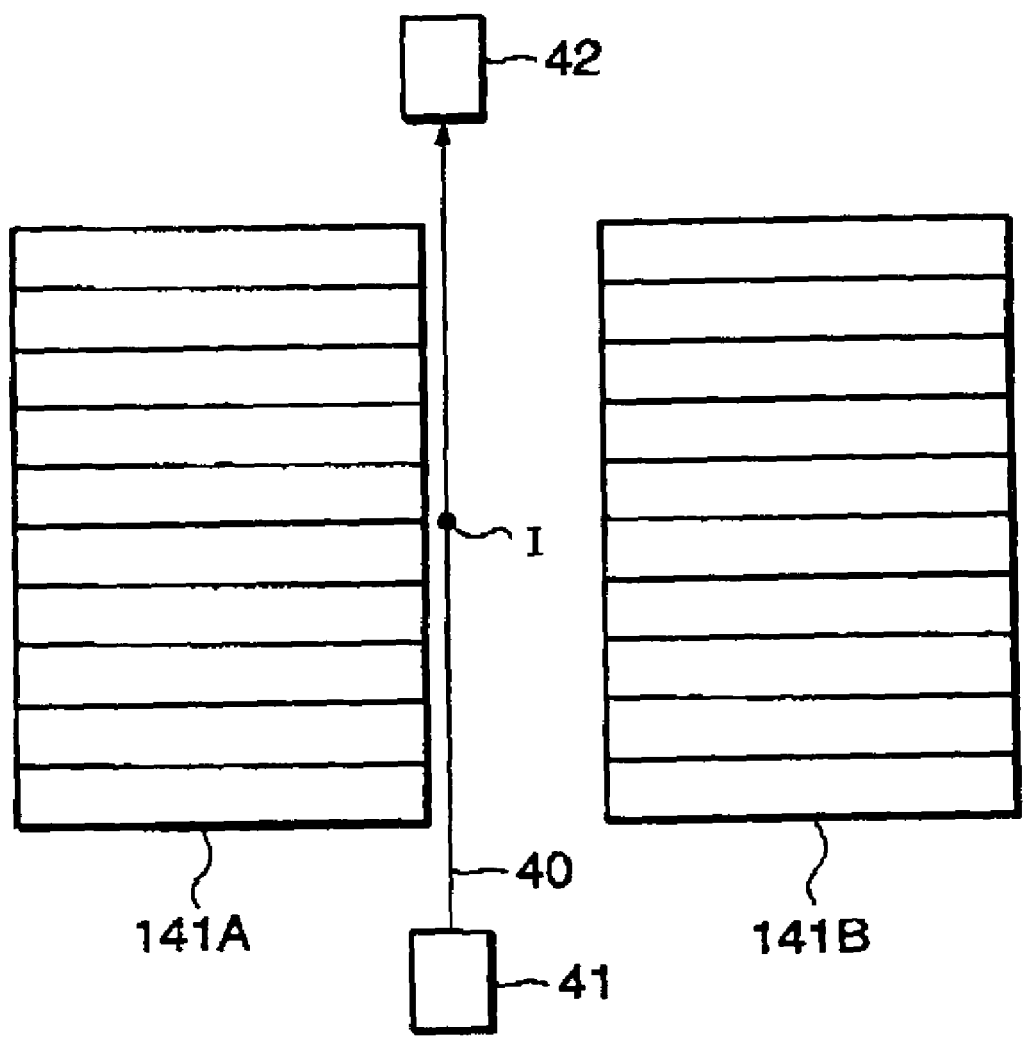
FIG. 20 is an illustration showing the second aspect of the collimating leaf position detection shown in FIG. 18 according to the second embodiment of the present invention.

When each collimating leaf of the collimating member 141A is moved towards the collimating member 141B, other position information may be used. As shown in FIG. 20, the laser beam generator 41 and the laser beam receiver 42 pair is placed where the laser beam 40 runs through the axis I. As described in the first embodiment, position information detected when each collimating leaf of the collimating member 141A is moved to intersect the laser beam 40 with one side close to the collimating member 141B may be used when the collimating leaf of the collimating member 141A is moved towards the collimating member 141B. Similarly, although not shown in FIG. 20, position information detected when each collimating leaf of the collimating member 141B is moved to intersect the laser beam 40 with one side close to the collimating member 141A may be used when the collimating leaf of the collimating member 141B is moved towards the collimating member 141A. Such a use of position information may be advantageous when the gear engagement is changed in accordance with the moving direction of each collimating leaf, as shown in FIG. 10.

Figure 21:
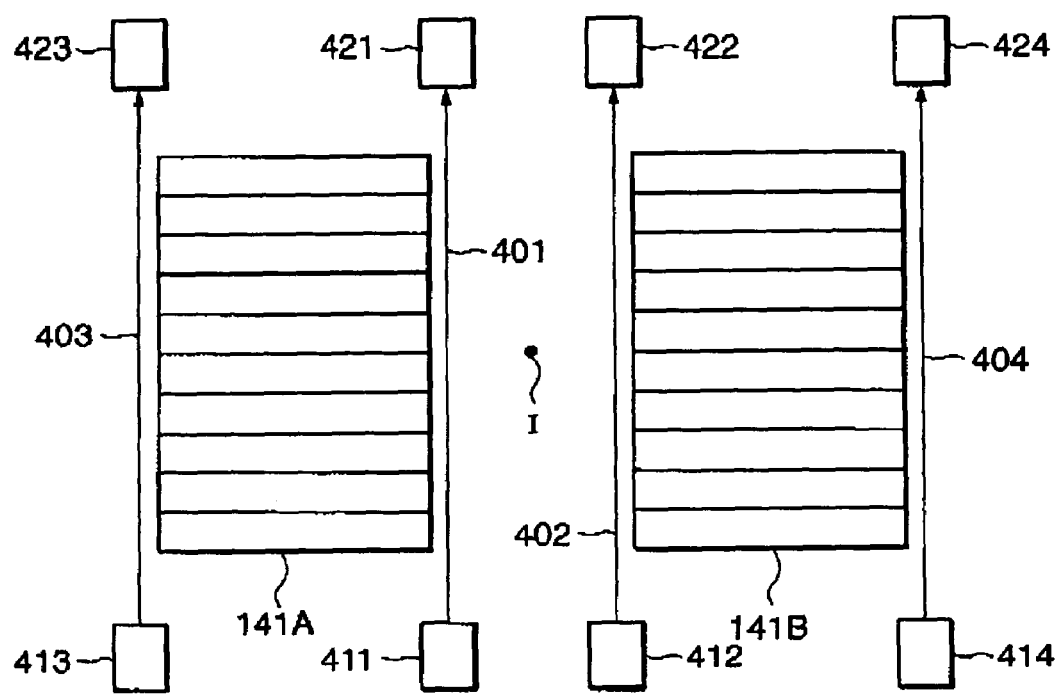
FIG. 21 is an illustration showing an example of the collimating leaf position detection with four laser beams according to the second embodiment of the present invention.

FIG. 21 is an illustration showing an example of the collimating leaf position detection with four laser beams according to the second embodiment of the present invention. As shown in FIG. 21, the laser beams 401 to 404 are generated from laser beam generators 411 to 414. The generated laser beams 401 to 404 are received by the laser beam receivers 421 to 424. In this configuration, the laser beam generator 413 and the laser beam receiver 423 pair can be placed anywhere one side of each collimating leaf of the collimating member 141A can intersect the laser beam 403. The one side is a side furthest from the collimating member 141B. One example of the placement is where the one side intersects the laser beam 403 when the collimating member 141A is moved furthest from the collimating member 141B, as shown in FIG. 19. Position information detected at this position regarding each collimating leaf may be used when the collimating leaf of the collimating member 141A is moved and positioned against the collimating member 141B.

Similarly, the laser beam generator 414 and the laser beam receiver 424 can be placed anywhere one side of each collimating leaf of the collimating member 141B can intersect the laser beam 404. The one side is a side furthest from the collimating member 141A. One example of the placement is where the one side intersects the laser beam 404 when the collimating member 141B is moved furthest from the collimating member 141B. Position information detected at this position regarding each collimating leaf may be used when the collimating leaf of the collimating member 141B is moved and positioned against the collimating member 141A.

Still in FIG. 21, the laser beam generator 411 and the laser beam receiver 421 pair can be placed between the collimating members 141A and 141B. For example, position information detected when each collimating leaf of the collimating member 141A is moved to intersect the laser beam 401 with one side closest to the collimating member 141B may be used when the collimating leaf of the collimating member 141A is moved and positioned towards the collimating member 141B. Similarly, the laser beam generator 412 and the laser beam receiver 422 pair can also be placed between the collimating members 141A and 141B. For example, position information detected when each collimating leaf of the collimating member 141B is moved to intersect the laser beam 402 with one side closest to the collimating member 141A may be used when the collimating leaf of the collimating member 141B is moved and positioned towards the collimating member 141A.

Figure 22:
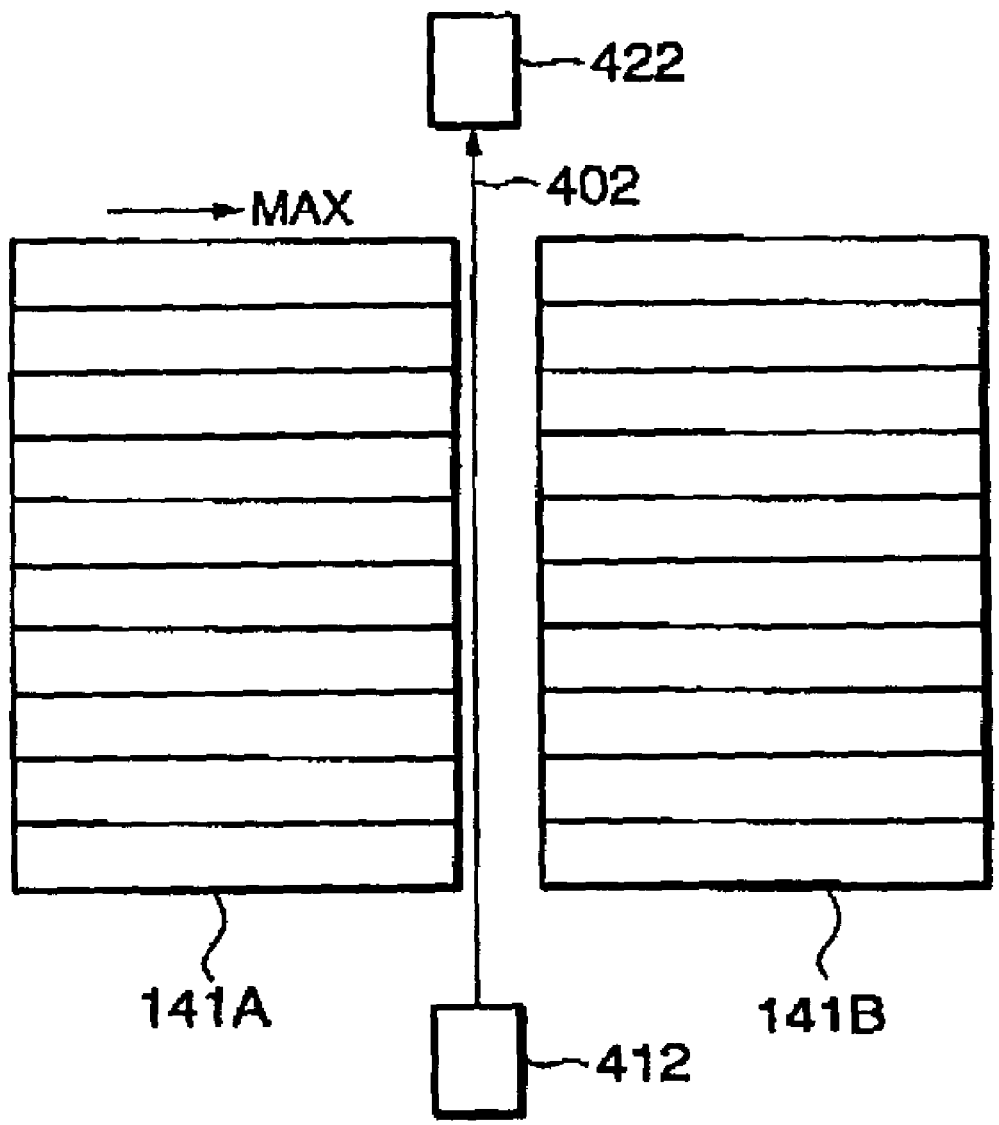
FIG. 22 is an illustration showing one aspect of the collimating leaf position detection shown in FIG. 21 according to the second embodiment of the present invention.

Although it depends on where the pair for the laser beam 401 and the pair for the laser beam 402 are placed, one of the pairs, for example the pair of the laser beam generator 412 and the laser beam receiver 422 for the laser beam 402, as shown in FIG. 22, can be placed where the laser beam 402 intersects one side closest to the collimating member 141B when each collimating leaf of the collimating member 141A is moved closest to the collimating member 141B. Position information detected at this position may be used when the collimating leaf of the collimating member 141A is moved and positioned towards the collimating member 141B. Similarly, although not shown in FIG. 22, one of the pairs, for example the pair of the laser beam generator 411 and the laser beam receiver 421 for the laser beam 401, can be placed where the laser beam 401 intersects one side closest to the collimating member 141A when each collimating leaf of the collimating member 141B is moved closest to the collimating member 141A. Position information detected at this position may be used when the collimating leaf of the collimating member 141B is moved and positioned towards the collimating member 141A. Such a use of position information may be advantageous when the gear engagement is changed in accordance with the moving direction of each collimating leaf, as shown in. FIG. 10.

Figure 23:
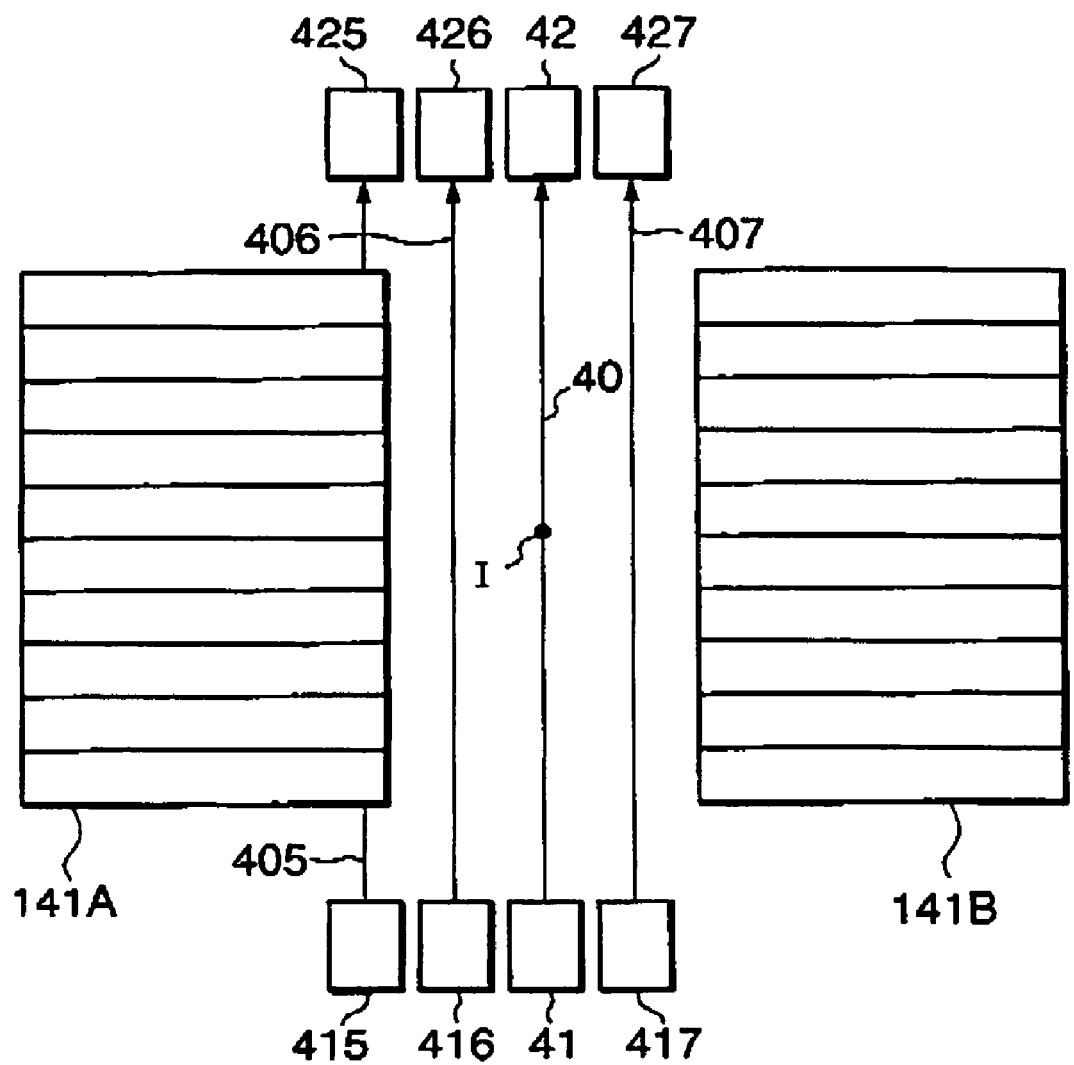
FIG. 23 is an illustration showing an example of the collimating leaf position detection with four laser beams for each collimating leaf according to the second embodiment of the present invention.

FIG. 23 is an illustration showing an example of the collimating leaf position detection with four laser beams for each collimating leaf according to the second embodiment of the present invention. As shown in FIG. 23, laser beams 405 to 407 generated from laser beam generators 415 to 417 are received by laser beam receivers 425 to 427, respectively. The laser beams 406 to 407 emanate between the collimating members 141A and 141B. In addition, the laser beam generator 41 and the laser beam receiver 42 pair can be placed so that the laser beam 40 runs through the axis I and between the collimating members 141A and 141B. These laser beams 40 and 405 to 407 may be used to a plurality of reference positions for each collimating leaf of the collimating member 141A. For example, an interval between adjacent laser beams may be the same. The laser beam 407 may run where each collimating leaf of the collimating member 141A is moved closest to the collimating member 141B. Also for example, the laser beam 405 may run where each collimating leaf of the collimating member 141A is moved furthest from the collimating member 141B. The laser beam 40 does not have to run through the axis I. Although not shown in FIG. 23, a similar detection technique can be applied to the position detection of each collimating leaf of the collimating member 141B. The technique shown in FIG. 23 may realize more accurate detection.

According to the embodiments of the present invention, the shape of each collimating leaf is not limited to an arc but can be any possible shape. Also the moving direction of each collimating leaf is not limited to a direction along a circular arc centered about an X-ray source but can be any direction, for example, a horizontal direction.

In the above embodiments of the present invention, the collimating members 140A and 140B have not been described as including a plurality of collimating leaves. When, however, each of the collimating members 140A and 140B includes a plurality of collimating leaves, the above embodiments of the present invention can also be applied to positioning of such collimating leaves.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the present invention may be practiced otherwise than as specifically described herein.

The invention claimed is:

1. A collimating device for controlling a radiation field of an X-ray radiated from an X-ray radiator, the device comprising:
    a first plurality of collimating leaves;
    a second plurality of collimating leaves opposing the first plurality of collimating leaves;
    a laser beam generator configured to generate a laser beam which emanates between the first and second plurality of collimating leaves, the laser beam having an axis perpendicular to an axis of the radiated X-ray between the first and second plurality of collimating leaves;
    a detector configured to detect the laser beam;
    a memory configured to store position information of each leaf of the first and second plurality of collimating leaves when said each leaf is determined to intersect the laser beam based on the detection; and
    a controller configured to position said each leaf based on the position information to control the radiation field.

2. The device according to claim 1, further comprising:
    a reflector configured to reflect the laser beam generated by the laser beam generator so that the reflected laser beam emanates between the first and second plurality of collimating leaves.

3. The device according to claim 1, further comprising:
    a reflector configured to reflect the laser beam emanated between the first and second plurality of collimating leaves so that the reflected laser beam is detected by the detector.

4. The device according to claim 1, wherein
the memory stores the position information when the detector detects a predetermined percentage of the laser beam.

5. The device according to claim 1, further comprising:
    a compensation unit configured to compensate the position information, wherein the controller positions said each leaf based on the compensated position information.

6. The device according to claim 5, wherein
the compensation unit compensates the position information in accordance with an incident angle of the laser beam between the first and second plurality of collimating leaves.

7. The device according to claim 5, wherein
the memory is further configured to store the compensated position information.

8. The device according to claim 1, further comprising:
    a second memory configured to store compensation distance information for compensating the position information, wherein the compensation distance information is based on a distance caused by a gear engagement in a gear rotation when said each leaf is driven by a gear.

9. The device according to claim 8, wherein
the second memory stores first distance information and second distance information as the compensation distance information;
the first distance information is used when said each leaf is driven to move by a first predetermined distance in a first direction; and
the second distance information is used when said each leaf is driven to move by a second predetermined distance in a second direction.

10. A collimating device for controlling a radiation field of an X-ray radiated from an X-ray radiator, the device comprising:
    a first plurality of collimating leaves;
    a second plurality of collimating leaves opposing the first plurality of collimating leaves;
    a laser beam generator configured to generate at least first and second laser beams, wherein the first laser beam extends alone a first axis to intersect the first plurality of collimating leaves and the second laser beam extends along a second axis to intersect the second plurality of collimating leaves, wherein the first and second axis are perpendicular to an axis of the radiated X-ray;
    a detector configured to detect the first and second laser beams;
    a memory configured to store first position information of each leaf of said first plurality of collimating leaves when each leaf of said first plurality of collimating leaves is determined to intersect the first laser beam based on the detection;
    said memory further configured to store second position information of each leaf of said second plurality of collimating leaves when each leaf of said second plurality of collimating leaves is determined to intersect the second laser beam based on the detection; and
    a controller configured to position said each leaf of said first plurality of collimating leaves based on the first position information and the each leaf of said second plurality of collimating leaves based on the second position information so as to control the radiation field.

11. The device according to claim 10, wherein
the laser beam generator generates a third laser beam which emanates between the first and second plurality of collimating leaves, the third laser beam having an axis perpendicular to an axis of the radiated X-ray between the first and second plurality of collimating leaves;
the detector is further configured to detect the third laser beam;
the memory is further configured to store third position information of each leaf of the first and second plurality of collimating leaves when said each leaf is determined to intersect the third laser beam based on the detection; and
the controller is configured to position said each leaf based on the third position information in addition to the first and second position information.

12. The device according to claim 10, wherein
the laser beam generator generates third and fourth laser beams which emanate between the first plurality of collimating leaves and the second plurality of collimating leaves, the third laser beam extends along a third axis to intersect the first plurality of collimating leaves and the fourth laser beam extends along a first axis to intersect the second plurality of collimating leaves, wherein the third and fourth axis are perpendicular to an axis of the radiated X-ray;

the detector is further configured to detect the third and fourth laser beams;

the memory is further configured to store the first position information when said each leaf of the first plurality of collimating leaves is positioned furthest from the second plurality of collimating leaves and determined to intersect the first laser beam with one side far from the second plurality of collimating leaves based on the detection;

said memory further configured to store the second position information when said each leaf of the second plurality of collimating leaves is positioned furthest from the first plurality of collimating leaves and determined to intersect the second laser beam with one side furthest from the first plurality of collimating leaves based on the detection;

said memory further configured to store third position information when said each leaf of said first plurality of collimating leaves is positioned closest to the second plurality of collimating leaves and determined to intersect the third laser beam with another side closest to the second plurality of collimating leaves based on the detection;

said memory further configured to store fourth position information when said each leaf of said second plurality of collimating leaves is positioned closest to the first plurality of collimating leaves and determined to intersect the fourth laser beam with another side closest to the first collimating leaves based on the detection; and the controller is configured to position said each leaf of said first plurality of collimating leaves based on the first and third position information and the said each leaf of said second plurality of collimating leaves based on the second and fourth position information.

13. The device according to claim 10, wherein the laser beam generator generates a first group of laser beams including the first laser beam and a second group of laser beams including the second laser beam as the plurality of laser beams, the first group of laser beams extends along a third axis to intersect the first plurality of collimating leaves and the second group of laser beams extends along a fourth axis to intersect the second plurality of collimating leaves, wherein the third and fourth axis are perpendicular to an axis of the radiated X-ray;

the detector is further configured to detect the first and second groups of laser beams;

the memory configured to store first information of positions of each leaf of said first plurality of collimating leaves where said each leaf of said first plurality of collimating leaves is determined to intersect the first group of laser beams with one side close to the second plurality of collimating leaves based on the detection;

said memory further configured to store second information of positions of each leaf of said second plurality of collimating leaves where said each leaf of said second plurality of collimating leaves is determined to intersect the second group of laser beams with one side close to the first plurality of collimating leaves based on the detection; and a controller configured to position said each leaf of said first plurality of collimating leaves based on the first information and said each leaf of said second plurality of collimating leaves based on the second information.

14. A radiotherapy apparatus for radiating an X-ray and concentrating the X-ray towards a predetermined part of an object, the apparatus comprising:

an X-ray radiator configured to radiate the X-ray; and a collimator configured to control a radiation field of the X-ray radiated by the X-ray radiator, including:

a first plurality of collimating leaves;

a second plurality of collimating leaves opposing the first plurality of collimating leaves;

a laser beam generator configured to generate a laser beam which emanates between the first and second plurality of collimating leaves, the laser beam having an axis perpendicular to an axis of the radiated X-ray between the first and second plurality of collimating leaves;

a detector configured to detect the laser beam;

a memory configured to store position information of each leaf of the first and second plurality of collimating leaves when said each leaf is determined to intersect the laser beam based on the detection; and a controller configured to position said each leaf based on the position information.

15. The apparatus according to claim 14, further comprising:

a display configured to display information of the collimator.

16. The apparatus according to claim 14, wherein the laser beam generator is rendered operative when said apparatus is powered.

17. The apparatus according to claim 14, wherein the laser beam generator is rendered operative at predetermined intervals.

18. The apparatus according to claim 14, further comprising an input unit configured to input an instruction, wherein the laser beam generator is rendered operative in response to the instruction.

19. A method of positioning collimating leaves for use in a collimator which controls a radiation field of an X-ray radiated from an X-ray radiator, wherein the collimating leaves include a first and second plurality of collimating leaves, said plurality of second collimating leaves opposing the first plurality of collimating leaves, the method comprising:

generating a laser beam which emanates between the first and second plurality of collimating leaves, the laser beam having an axis perpendicular to an axis of the radiated X-ray between the first and second plurality of collimating leaves;

detecting the laser beam;

storing position information of each leaf of the first and second plurality of collimating leaves when said each leaf is determined to intersect the laser beam based on the detection; and positioning said each leaf based on the position information to control the radiation field.

20. A method of positioning collimating leaves for use in a collimator which controls a radiation field of an X-ray radiated from an X-ray radiator, wherein the collimating leaves include a first and second plurality of collimating leaves, the plurality of second collimating leaves opposing the first plurality of collimating leaves, the method comprising:

generating at least first and second laser beams, wherein the first laser beam extends along a first axis to intersect the first plurality of collimating leaves and the second laser beam extends along a second axis to intersect the second plurality of collimating leaves, wherein the first and second axis are perpendicular to an axis of the radiated X-ray;

detecting the first and second laser beams;

storing first position information of each leaf of said first plurality of collimating leaves when said each leaf of said first plurality of collimating leaves is determined to intersect the first laser beam based on the detection and storing second position information when each leaf of said second plurality of collimating leaves is determined to intersect the second laser beam based on the detection; and positioning said each leaf of said first plurality of collimating leaves based on the first position information and said each leaf of said second plurality of collimating leaves based on the second position information to control the radiation field.

* * * * *